United States Patent
Ebetino et al.

(10) Patent No.: US 10,857,165 B2
(45) Date of Patent: Dec. 8, 2020

(54) SKELETAL REMOVAL OF BISPHOSPHONATES

(71) Applicants: The Regents of the University of California, Oakland, CA (US); BioVinc LLC, Pasadena, CA (US); University of Southern California, Los Angeles, CA (US)

(72) Inventors: Frank Hallock Ebetino, Venice, FL (US); Ichiro Nishimura, Venice, CA (US); Shuting Sun, Temple City, CA (US); Mark Walden Lundy, Cincinnati, OH (US); Akishige Hokugo, Los Angeles, CA (US); Charles McKenna, Pacific Palisades, CA (US); Keivan Sadrerafi, Pasadena, CA (US)

(73) Assignees: The Regents of the University of California, Los Angeles, CA (US); BioVinc LLC, Pasadena, CA (US); University of Southern California, Los Angeles, CA (US)

(*) Notice: Subject to any disclaimer, the term of this patent is extended or adjusted under 35 U.S.C. 154(b) by 0 days.

(21) Appl. No.: 16/099,227

(22) PCT Filed: May 31, 2017

(86) PCT No.: PCT/US2017/035169
§ 371 (c)(1),
(2) Date: Nov. 6, 2018

(87) PCT Pub. No.: WO2017/210272
PCT Pub. Date: Dec. 7, 2017

(65) Prior Publication Data
US 2019/0209590 A1    Jul. 11, 2019

Related U.S. Application Data
(60) Provisional application No. 62/344,245, filed on Jun. 1, 2016.

(51) Int. Cl.
*A61K 31/675* (2006.01)
*A61K 31/663* (2006.01)
(Continued)

(52) U.S. Cl.
CPC ............ *A61K 31/663* (2013.01); *A61K 9/006* (2013.01); *A61K 31/675* (2013.01); *A61P 19/08* (2018.01); *C07F 9/58* (2013.01); *C07F 9/6506* (2013.01); *C07F 9/6561* (2013.01); *C07F 9/65583* (2013.01); *C07F 9/65586* (2013.01)

(58) Field of Classification Search
CPC .................................................. A61K 31/675
See application file for complete search history.

(56) References Cited

PUBLICATIONS

Zahrowski (American Journal of Orthodontics and Dentofacial Orthopedics, vol. 131, Iss 3, Mar. 2007, pp. 311-320). (Year: 2007).*

(Continued)

*Primary Examiner* — Benjamin J Packard
(74) *Attorney, Agent, or Firm* — Suzannah K. Sundby, Esq.; Canady + Lortz LLP

(57) ABSTRACT

Disclosed herein are methods and compositions for removing or displacing bisphosphonates in skeletal tissue.

20 Claims, 28 Drawing Sheets

(51) Int. Cl.
  C07F 9/58 (2006.01)
  C07F 9/6561 (2006.01)
  C07F 9/6558 (2006.01)
  C07F 9/6506 (2006.01)
  A61P 19/08 (2006.01)
  A61K 9/00 (2006.01)

(56) References Cited

PUBLICATIONS

International Search Report received in PCT/US2017/035169 dated Aug. 11, 2017.

Written Opinion received in PCT/US2017/035169 dated Aug. 11, 2017.

Bae et al., "Development of oral osteomucosal tissue constructs in vitro and localization of fluorescently-labeled pisphosphonates to hard and soft tissue", Aug. 2014, pp. 559-563, vol. 34, No. 2, Publisher: Int J Mol Med.

Hokugo et al., "Equilibrium-dependent bisphosphonate interaction with crystalline bone mineral explains anti--esorptive pharmacokinetics and prevalence of osteonecros", Mar. 1, 2013, pp. 59-68, vol. 53, No. 1, Publisher: Bone.

Hokugo et al., "https://iadr2017.zerista.com/event/member/331809", "BRONJ Prevention by Competitive Equilibrium-based Displacement of Bisphosphonates in Mice", Mar. 24, 2017, Publisher: 95th General Session & Exhibition of the International Association for Dental Research.

Ikeda et al., "Successful treatment of Bisphosphonate-Related Osteonecrosis of the Jaw (BRONJ) patients with sitafloxacin: New strategies for the treatment of BRONJ", Dec. 27, 2014, pp. 217-222, vol. 73, Publisher: Bone.

Oizumi et al., "Inhibition of necrotic actions of nitrogen-containing bisphosphonates (NBPs) and their elimination from bone by etidronate (a non-NBP) . . . ", May 2010, pp. 1043-1054, vol. 68, No. 5, Publisher: J Oral Maxillofac Surg.

Oizumi et al., "Necrotic actions of nitrogen-containing bisphosphonates and their inhibition by clodronate, a non-nitrogen-containing bisphosphonate in mice . . . ", May 2009, pp. 384-392, vol. 104, No. 5, Publisher: Basic Clin Pharmacol Toxicol.

Okada et al., "Inhibition of Phosphate Transporters Ameliorates the Inflammatory and Necrotic Side Effects of the Nitrogen-Containing Bisphosphonate Zoledronate . . . ", Oct. 2013, pp. 145-158, vol. 231, No. 2, Publisher: The Tohoku Journal of Experimental Medicine.

Roelofs et al., "Influence of bone affinity on the skeletal distribution of fluorescently labeled bisphosphonates in vivo", Apr. 2012, pp. 835-847, vol. 27, No. 4, Publisher: J Bone Miner Res.

Russell et al., "An Update on Mechanisms of Action and How These Relate to Clinical Efficacy", Bisphosphonates, Nov. 28, 2007, pp. 209-257, vol. 1117, Publisher: Annals of the New York Academy of Sciences.

Sun et al., "Fluorescent Bisphosphonate and Carboxyphosphonate Probes: A Versatile Imaging Toolkit for Applications in Bone Biology and Biomedicine", Feb. 17, 2016, pp. 329-340, vol. 27, No. 2, Publisher: Bioconjugate Chemistry.

Yamaguchi et al., "Osteonecrosis of the jawbones in 2 osteoporosis patients treated with nitrogen-containing bisphosphonates: osteonecrosis reduction replacing NBP . . . ", Apr. 2010, pp. 889-897, vol. 68, No. 4, Publisher: J Oral Maxillofac Surg.

* cited by examiner

Kd = 8.754 ± 1.251 μM

Bmax = 0.8437 ± 0.02790 μmol/m$^2$

Kd= 53.20 ± 28.90 μM

Bmax= 0.4467 ± 0.08379 μmol/m$^2$

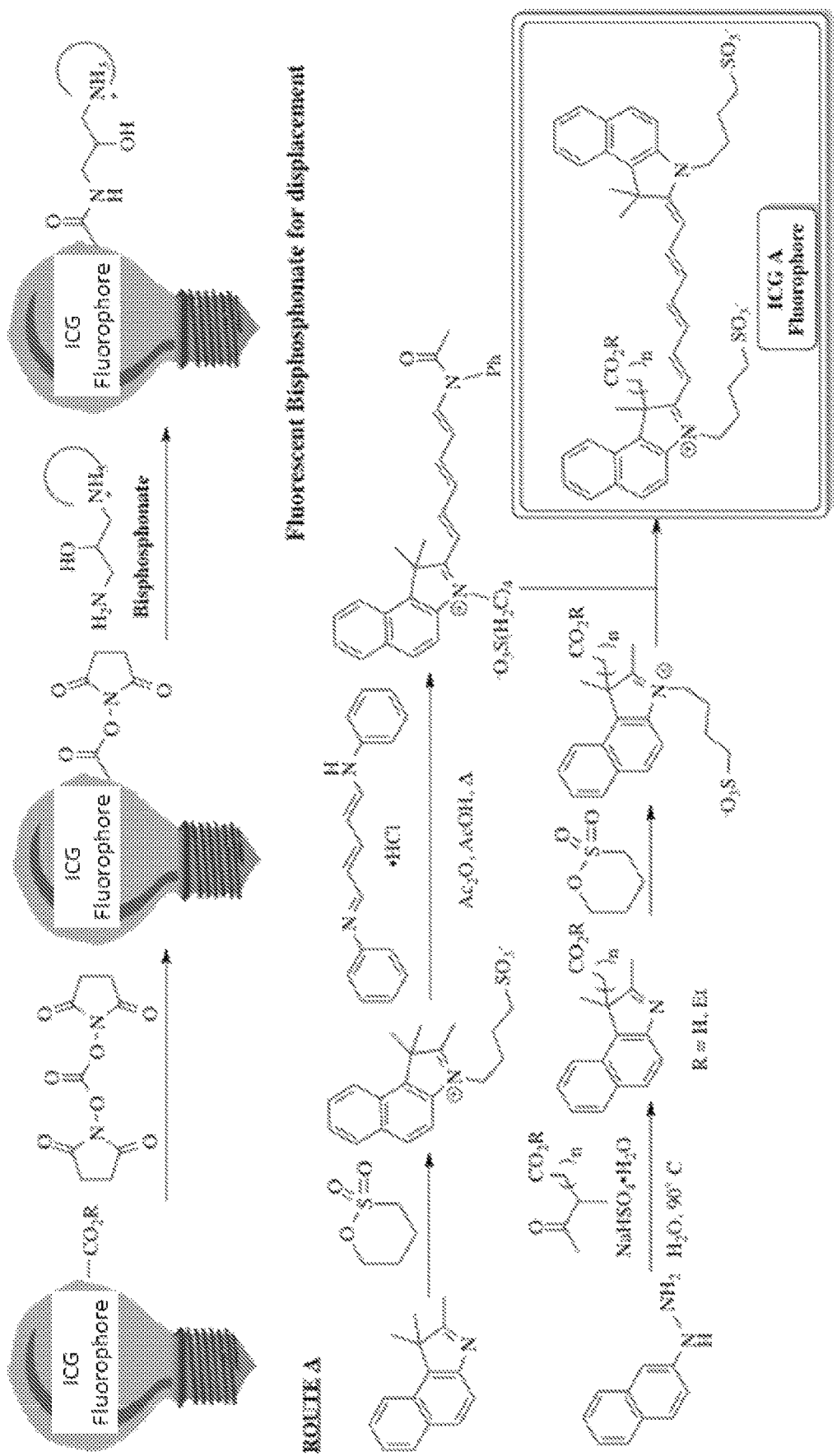
Figure 18A1

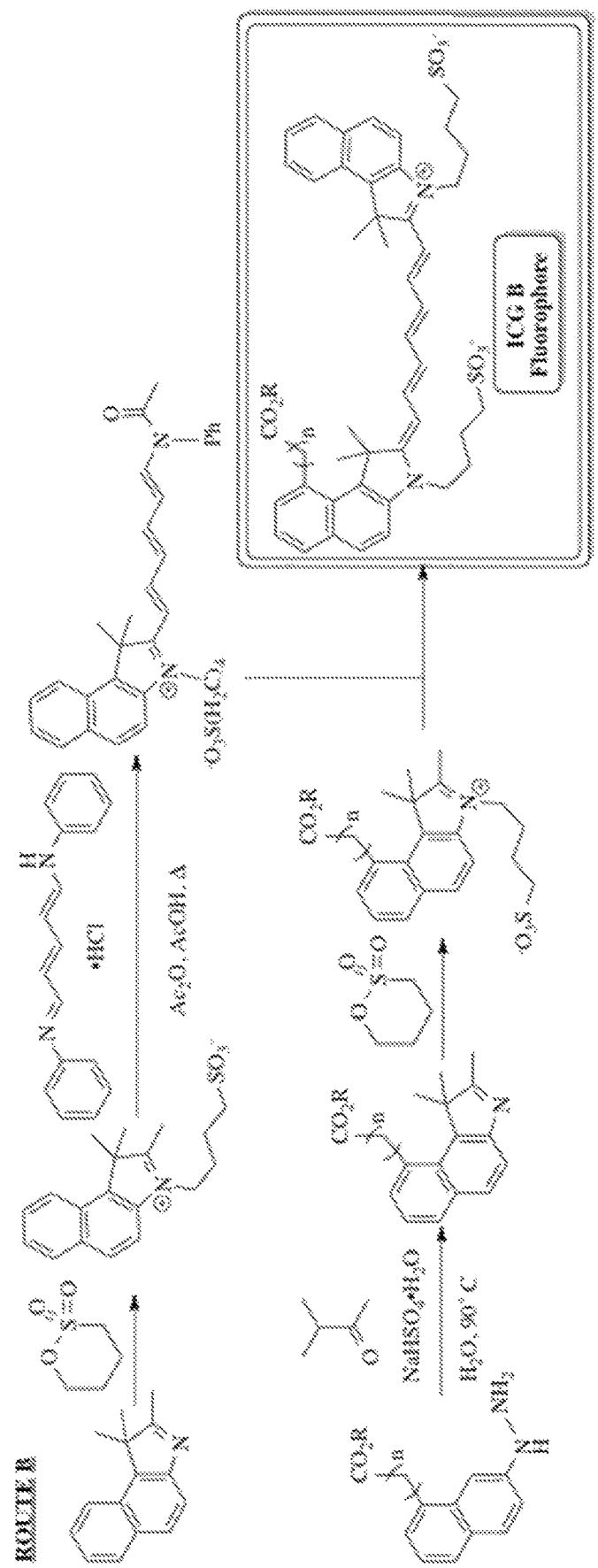
Figure 18A2

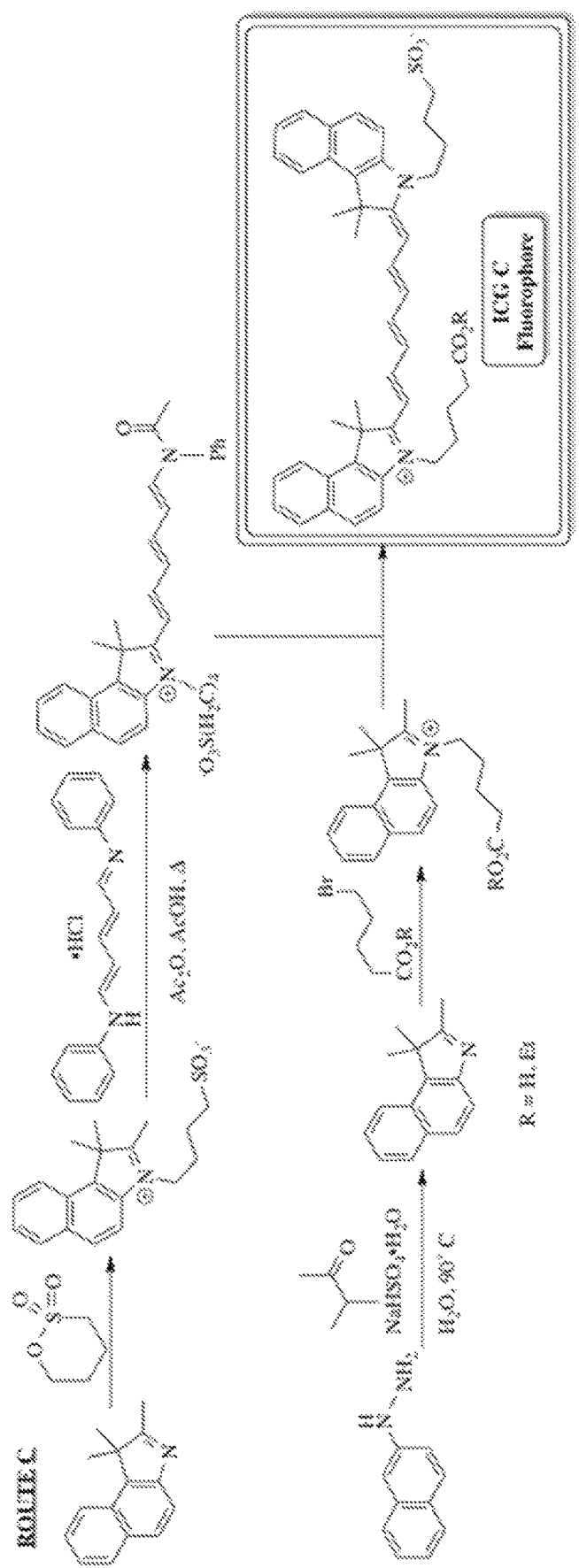
Figure 18A3

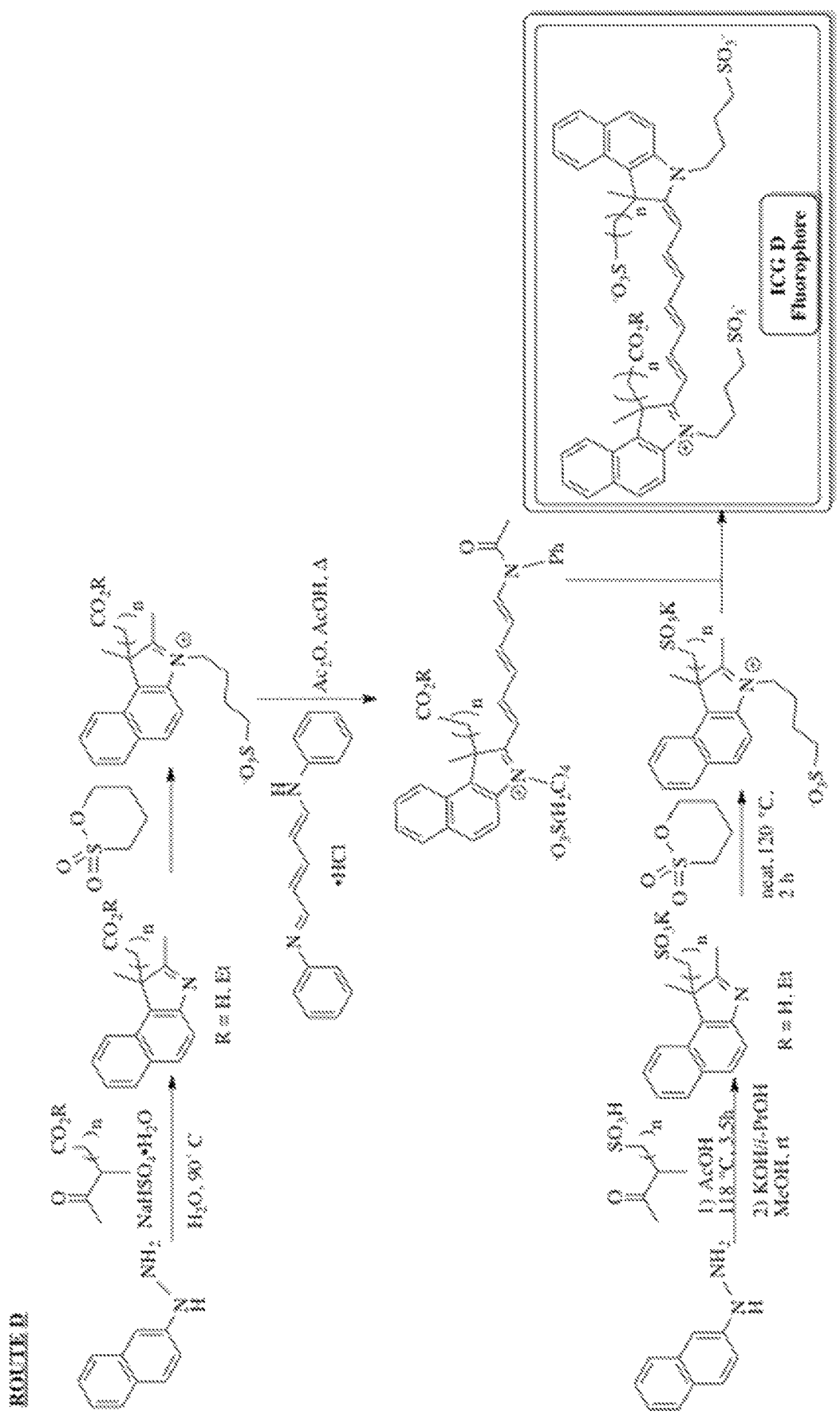
Figure 18A4

SKELETAL REMOVAL OF BISPHOSPHONATES

ACKNOWLEDGEMENT OF GOVERNMENT SUPPORT

This invention was made with Government support under Grant Nos. DE022552, DE023410, DE025524 awarded by the National Institutes of Health. The Government has certain rights in the invention.

BACKGROUND OF THE INVENTION

1. Field of the Invention

The present invention relates to methods of treating osteonecrosis and other skeletal disorders and symptoms, including Bisphosphonate Related Osteonecrosis of the Jaw (BRONJ).

2. Description of the Related Art

Osteonecrosis of the jaw (ONJ) is a rare but severe oral complication, which is characterized by symptoms consisting painful bone exposure or fistulation that do not resolve over several months to years. It was initially described as Bisphosphonate Related ONJ (BRONJ), when identified in patients treated with potent antiresorptive bisphosphonate (BP) drugs, particularly nitrogen-containing BPs (N-BPs) such as zoledronate (ZOL), pamidronate, and alendronate, and was also found later in some patients taking other antiresorptive or antiangiogenic medications, such as denosumab. In some cases, ablation surgery of necrotic oral and maxillofacial bones has been required, significantly affecting patients' life quality, however, current preventive and treatment modalities are limited. Clinical reports and patient surveys have indicated that dental procedures such as routine tooth extraction and denture wearing markedly increase the risk of developing ONJ, thus causing uncertainty and apprehension among dental healthcare professionals and patients in recent years.

The updated position paper released by American Association of Oral and Maxillofacial Surgeons (AAOMS) redefined ONJ as Medication Related Osteonecrosis of the Jaw (MRONJ), expanding the scope of its previous position paper on BRONJ. MRONJ reflects the inclusion of ONJ resulting from or associated with the administration of medications in addition to active BPs, for example, receptor activator of nuclear factor kappa-B ligand (RANKL) inhibitors (e.g., denosumab) and antiangiogenic therapies as possible associated agents.

The mechanisms of action of active BPs and denosumab are considered by those skilled in the art to be different. The pharmacological mechanism of active BPs is based on their resemblance to pyrophosphate. Because of a high affinity for calcium ions in the bone, active BPs accumulate on the bone and targets osteoclasts. During bone resorption, active BPs are endocytosed by osteoclasts, and inhibit an important enzyme, farnesyl pyrophosphate synthase, in the mevalonate pathway. As a result, the activity of osteoclasts is decreased, leading to the reduction of bone loss. By contrast, denosumab inhibits RANKL, a protein that binds to the RANK receptors on the pre-osteoclasts. Denosumab prevents RANKL from binding to RANK receptors, thus impairing osteoclast formation.

A "drug holiday" has been recommended by AAOMS as a possible preventive measure for the patients and has shown some promising results in patients with denosumab therapy; however, its effectiveness for patients who have been treated with active BPs has not been well established, which may partially due to their different mechanisms of actions and the prolonged half-lives of active BPs in bone. After administration, as much as about 50% of an active BP is incorporated into bone and the rest is rapidly excreted through the kidneys. There is no systemic metabolism of active BPs, contributing to their prolonged half-lives, which may reach several months to over 10 years depending on the given BP. In fact, the US FDA determined that there was "no substantial data available to guide decisions regarding the initiation or duration of a drug holiday".

Because active BPs have been marketed for nearly 15 years, there are numerous patients who have been treated with active BPs and may have the active BPs retained in their skeletal systems. Therefore, BRONJ continues to present a healthcare threat to many who were and are treated with active BPs.

Thus, a need exists for methods of treating, preventing, and/or inhibiting BRONJ, as well as other bone and skeletal issues caused by or associated with treatment with active BPs.

SUMMARY OF THE INVENTION

In some embodiments, the present invention provides methods for removing or displacing an active BP in a skeletal tissue, such as bone tissue, which comprise administering to the skeletal tissue one or more inactive BPs. In some embodiments, the active BP in the skeletal tissue, such as bone tissue, is removed or displaced in vivo in a subject. In some embodiments, the present invention provides methods for treating, reducing, preventing, or inhibiting BRONJ and/or a bisphosphonate-related symptom in a subject, which comprises administering to the subject one or more inactive BPs. In some embodiments, the present invention is directed to use of one or more inactive BPs for removing or displacing an active BP in a skeletal tissue, such as bone tissue. In some embodiments, the present invention is directed to a medicament for the treatment of BRONJ and/or a bisphosphonate-related symptom, which comprises a therapeutically effective amount of one or more inactive BPs.

Examples of inactive BPs suitable for use in the various embodiments of the present invention include those described at paragraphs [0044] to [0050] and pharmaceutically acceptable salts, solvates, and prodrugs thereof and examples of active BPs include those described at paragraph [0043]. In some embodiments, the active BP being removed or displaced is an active nitrogen-containing bisphosphonate. In some embodiments, the active nitrogen-containing bisphosphonate is alendronate, ibandronate, minodronate, pamidronate, risedronate, or zoledronate. In some embodiments, the one or more inactive BPs is a low activity bisphosphonate. In some embodiments, the one or more inactive BPs lack an α-hydroxy group, have a pyridyl side chain that is para-substituted, and/or comprise a bisphosphonate covalently attached to a fluorescent compound. In some embodiments, the active BP being removed or displaced is an active nitrogen-containing bisphosphonate and the one or more inactive BPs is a low activity bisphosphonate. In some embodiments, the active nitrogen-containing bisphosphonate is alendronate, ibandronate, minodronate, pamidronate, risedronate, or zoledronate and the one or more inactive BPs is a low activity bisphosphonate. In some embodiments, the active nitrogen-containing bisphosphonate is alendronate, ibandronate, minodronate, pamidronate, risedronate, or zoledronate and the one or more inactive BPs lack an α-hydroxy group. In some embodiments, the active nitrogen-containing bisphosphonate is alendronate, ibandronate, minodronate, pamidronate, risedronate, or zoledronate and the one or more inactive BPs have a pyridyl side chain that is para-substituted. In some embodiments, the active nitrogen-containing bisphosphonate is alendronate, ibandronate, minodronate, pamidronate, risedronate, or zoledronate and the one or more inactive BPs lack an α-hydroxy group and/or have a pyridyl side chain that is para-substituted. In some embodiments, the active nitrogen-containing bisphosphonate is alendronate, ibandronate, minodronate, pamidronate, risedronate, or zoledronate and the one or more inactive BPs comprise a bisphosphonate covalently attached to a fluorescent compound. In embodiments where the mode of administration is systemic administration, the one or more inactive BPs is not etidronate. In some embodiments, the one or more inactive BPs has the following structure:

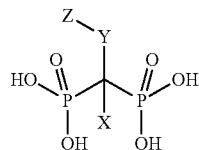

wherein X is H, hydroxyl, amino, halo, alkyl, or aryl; Y is hydroxyl, amino, alkyl, aryl, or heterocycle; and Z is a detectable label, such as a fluorophore, that may be present or absent. In some embodiments, X is a hydroxyl or H and Y is a pyridyl group that is para-substituted. In some embodiments, Z is present. In some embodiments, Z is absent.

In some embodiments of the methods of the present invention, the one or more inactive BPs is systemically administered to a subject, with the proviso that the one or more inactive BPs is not etidronate. In some embodiments, the one or more inactive BPs is locally administered to a site where the active BP is to be removed or displaced. In some embodiments, the one or more inactive BPs is administered orally to the subject. In some embodiments, the one or more inactive BPs is administered to a gingival tissue and/or a palatal tissue of the subject. In some embodiments, the one or more inactive BPs is administered by injection at the site where active BP is to be removed or displaced. In some embodiments, the one or more inactive BPs is administered topically at the site where active BP is to be removed or displaced. In some embodiments, the one or more inactive BPs is administered by intraoral application to the site of a dentoalveolar procedure performed on the subject. In some embodiments, the one or more inactive BPs is administered before, during, and/or after the dentoalveolar procedure. In some embodiments, the one or more inactive BPs is administered by direct injection into the mucosa at or near the site of a dentoalveolar procedure. In embodiments where the one or more inactive BPs being administered is etidronate, the mode of administration is local administration. In some embodiments, the one or more inactive BPs is administered as a pharmaceutical composition. In some embodiments, the one or more inactive BPs is provided in the form of a pharmaceutical composition. In some embodiments, the pharmaceutical composition is a composition or formulation as described at paragraphs [0064] to [0067]. In some embodiments, the pharmaceutical composition is a deformable nanovesicles formulation. In some embodiments, the pharmaceutical composition is a phospholipid-based deformable nanovesicles formulation. In some embodiments, an effective amount of the one or more inactive BPs is administered. In some embodiments, a therapeutically effective amount of the one or more inactive BPs is administered to the subject. In some embodiments, the subject who is administered the one or more inactive BPs has been treated with an active BP. In some embodiments, the subject who is administered the one or more inactive BPs is being treated with an active BP. In some embodiments, the subject who is administered the one or more inactive BPs will be treated with an active BP.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein:

FIG. 8A shows the adsorption isotherm for 5(6)-ROX-RIS, FIG. 8B shows the adsorption isotherm for 5(6)-ROX-RISPC, FIG. 8C shows the adsorption isotherm for AF647-RIS, and FIG. 8D shows the adsorption isotherm for AF647-RISPC.

FIG. 12A are fluorescent images of cranial bone. AF647-ZOL (50 μM) was pre-adsorbed on cranial bone via IV injection. 5-FAM-ZOL at the indicated doses was directly injected to the sub-periosteal space. FIG. 12B is a graph showing that the 5-FAM-ZOL signal increased with increasing injection dose, while the AF647-ZOL signal decreased. The first bars of each set are for AF647-ZOL and the second bars of each set are for 5-FAM-ZOL. *, P<0.05 vs Veh by Dunnett's test. FIG. 12C are images of cranial bone cryo-cross sections, which revealed localized displacement of AF647-ZOL and replacement by 5-FAM-ZOL.

FIG. 16A schematically shows the mouse model studies involving ZOL IV injection followed by tooth extraction. AF647-ZOL was applied by intra-oral injection or IV injection 1 day prior to tooth extraction. FIG. 16B are images of mouse maxilla and the oral mucosa inflammation and swelling (white dotted lines, left and right panels) with various degrees of jawbone exposure (arrow) at the tooth extraction site of ZOL-treated mice (BRONJ control: n–4). In the AF647-ZOL intra-oral injection group (n=4) (middle panel), all mice exhibited excellent tooth extraction wound healing without chronic inflammation or swelling. The AF647-ZOL IV injection group (n=4) (right panel) showed attenuated BRONJ-like lesions. FIG. 16C presents standardized fluorescent biophotonics images of mouse femurs showing that the AF647-ZOL signal could be clearly observed in femurs after AF647-ZOL IV injection. By contrast, intra-oral injection did not result in a detectable fluorescent signal in femurs.

FIG. 18A1 to FIG. 18A4 schematically present the preparation of ICG analogs for the synthesis of near infrared FL-BPs (ICG-BPs) that can be used for displacement of active BPs. FIG. 18A1 shows a general schematic and synthetic Route A, FIG. 18A2 shows synthetic Route B, FIG. 18A3 synthetic Route C, and FIG. 18A4 shows synthetic Route D.

FIG. 19A shows the results of micro CT evaluation of mouse femur trabecular structure demonstrating the lack of anti-resorptive effect of MHDP, which remained at the baseline level as the saline (0.9% NaCl) vehicle group. Zoledronate (ZOL) exhibited a significant anti-resorptive effect as shown in increased bone volume over tissue volume (BV/TV) and by decreased connectivity density (ConnD) in trabecular bone. FIG. 19B outlines the protocol for the experiments using MHDP to treat C57B16 mice. An ONJ-like lesion was generated by ZOL IV injection into the mouse, followed by extraction of the maxillary first molar. One day prior to the tooth extraction, a group of mice received intra-oral injection of 2 μg MHDP and another group received IV injection of 100 μg MHDP. FIG. 19C presents images of the mouse maxilla. The left panel shows that ZOL-injected mice without the MHDP treatment developed ONJ-like lesions: extensive inflammation of oral mucosa and exposed jawbone. Intra-oral injection (middle panel) and IV injection (right panel) of MHDP prevented the development of ONJ-like lesions.

DETAILED DESCRIPTION OF THE INVENTION

Figure 1:
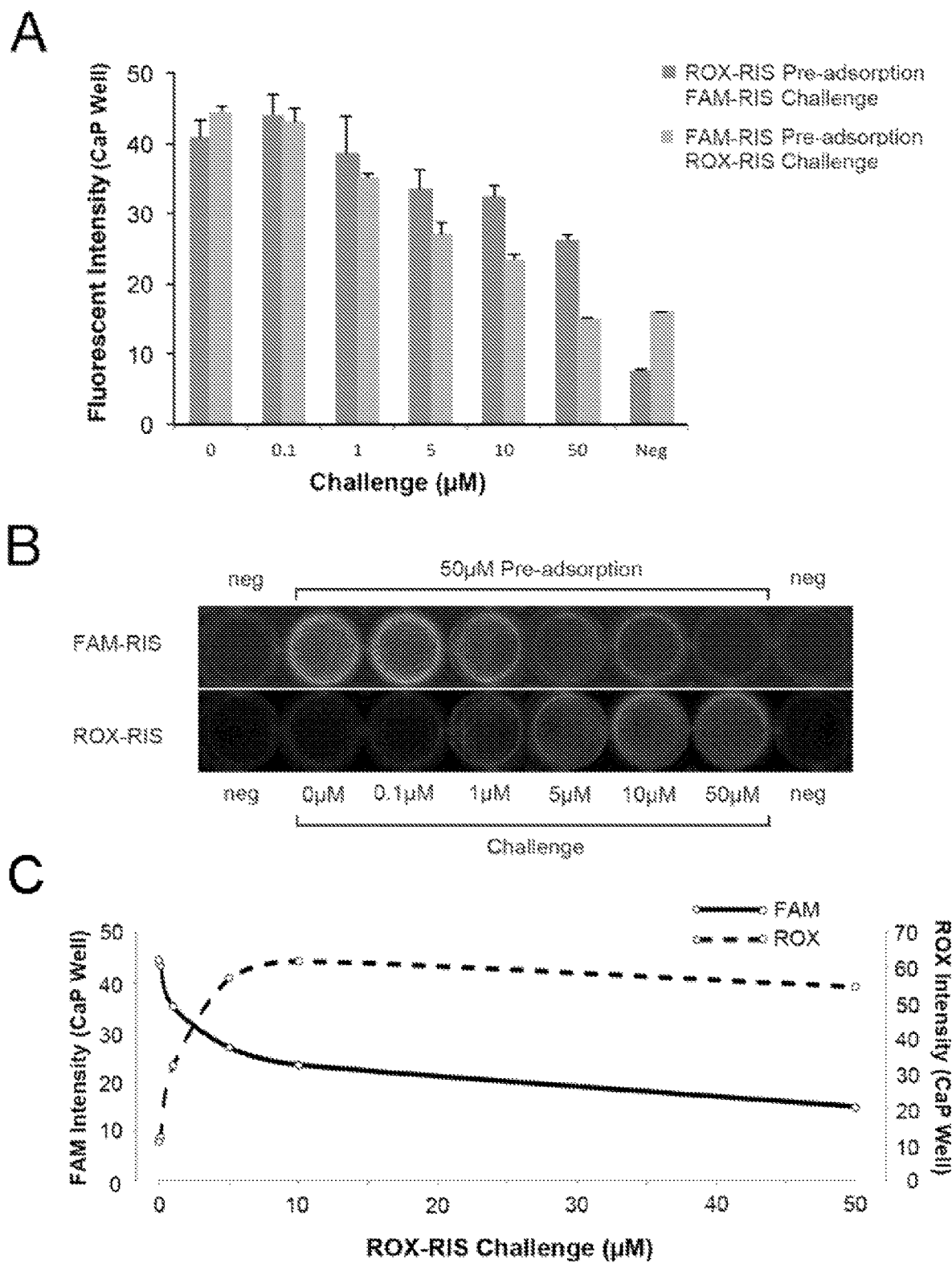
FIG. 1, Panels A-C, illustrates displacement of an adsorbed fluorescently labeled BP (FL-BP) from a hydroxyapatite surface mimicking bone by a different fluorescently labeled BP. Synthetic bone/dentine (calcium phosphate, CaP)-coated culture wells were pre-treated with either ROX-RIS or 5-FAM-RIS (50 μM). After challenged by serially diluted doses of 5-FAM-RIS or ROX-RIS (from 0 to 50 μM), respectively, Carboxyl-X-Rhodamine (ROX) and carboxyfluorescein (FAM) fluorescence intensities of the CaP-coated wells were measured. Panel A: ROX-RIS in CaP (first bars of each set) remained near the pre-adsorbed 50 μM level until 5 μM or greater concentrations of 5-FAM-RIS challenged. In contrast, 5-FAM-RIS (second bars of each set) was rapidly displaced by concentrations of ROX-RIS as low as 1 μM. Panel B: Pre-adsorbed FAM-RIS was replaced by ROX-RIS between 10 μM to 50 μM. Panel C: The quantitative measurement of FAM and ROX fluorescent signals was conducted by standardized fluorescent biophotonics and a proprietary program (LAS3000, FUJIFILM, Tokyo, Japan).
Figure 2A:
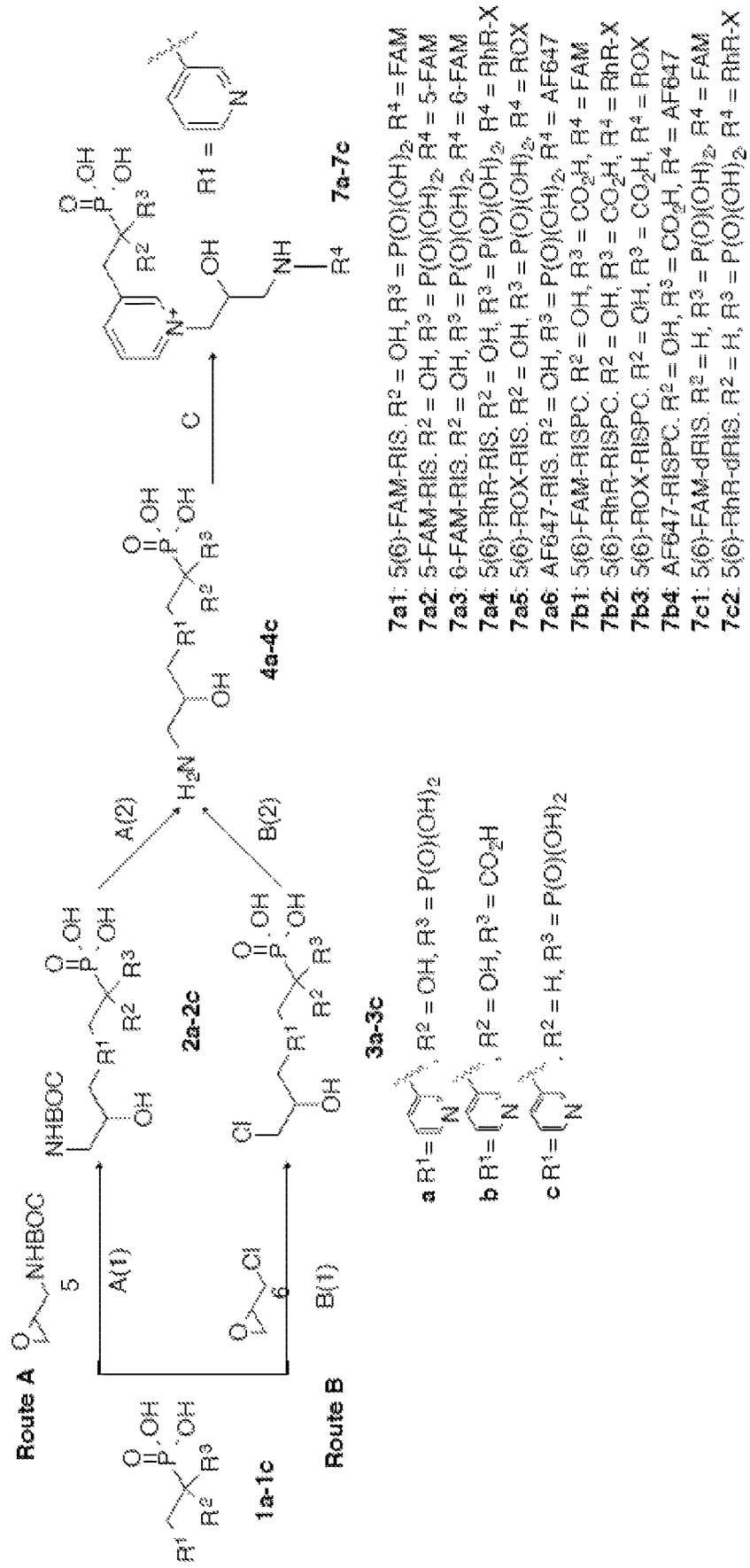
FIG. 2A, FIG. 2B, FIG. 2C, and FIG. 2D schematically show the synthesis of various FL-BPs.
Figure 2B:
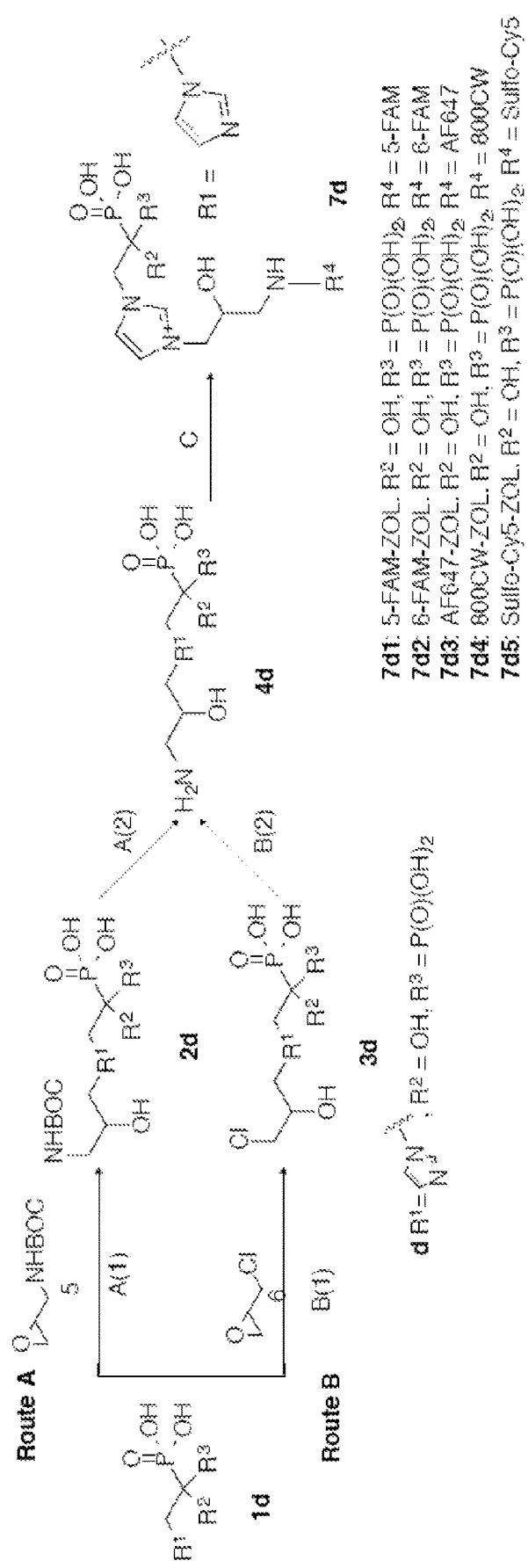
Figure 2C:
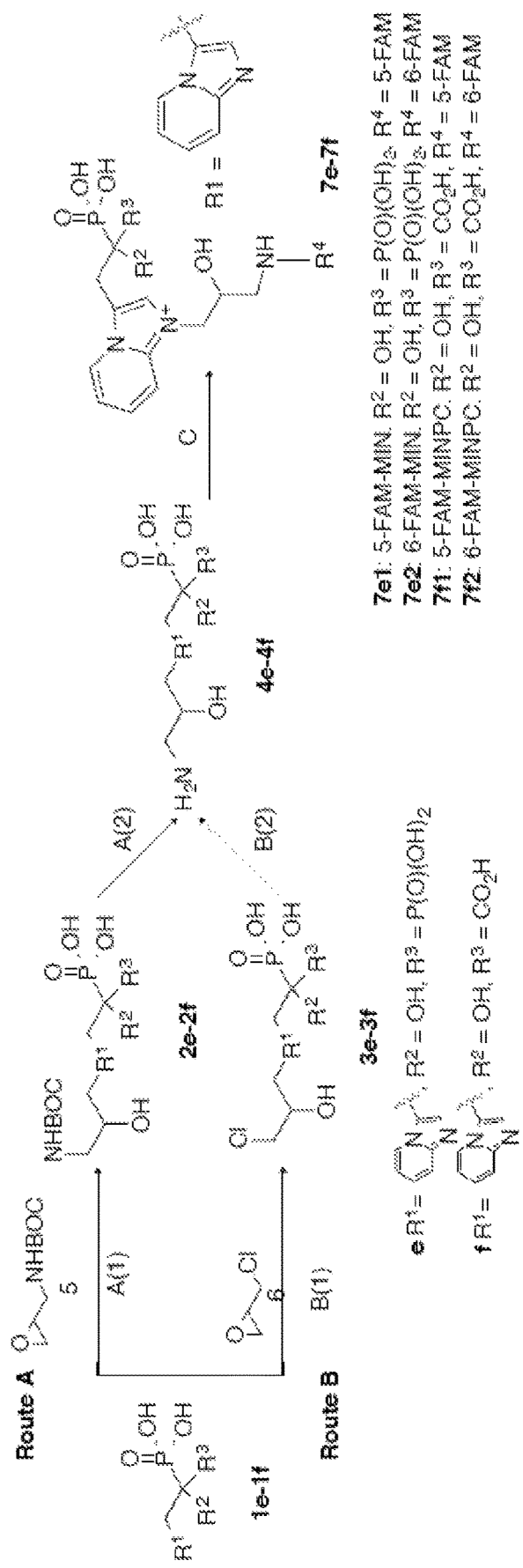
Figure 2D:
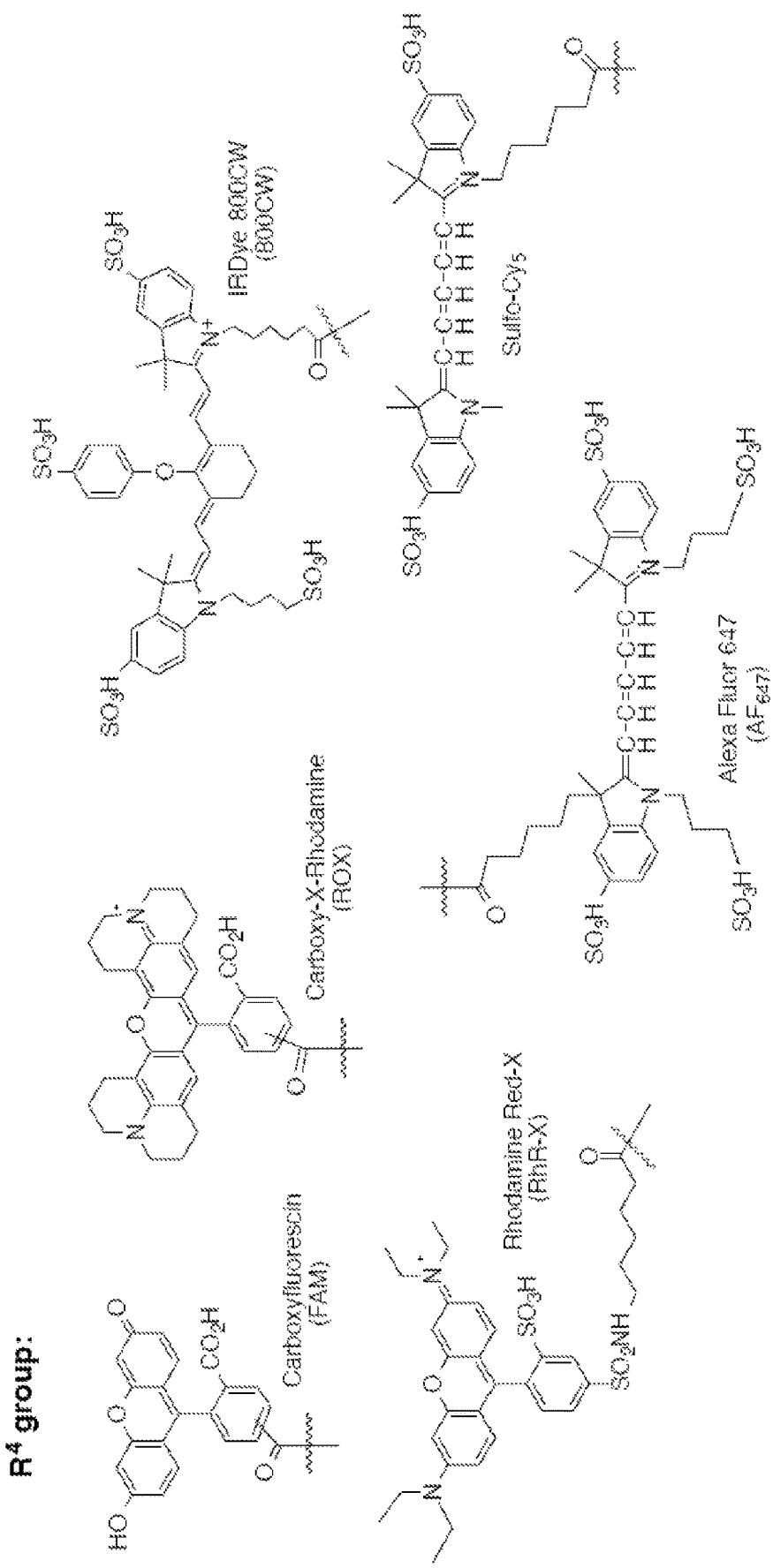

Medication-related osteonecrosis of the jaw (MRONJ) is clinically characterized as unresolved exposure of or fistula communication to partially necrotic jawbone in the oral cavity and is frequently associated with dentoalveolar procedures. Among the antiresorptive and antiangiogenic medications, treatment with antiresorptive bisphosphonates is prominently associated with reported clinical cases of MRONJ. Repeated administration of antiresorptive bisphosphonates result in high accumulation levels of the antiresorptive bisphosphonates in bone that are often associated with osteonecrosis of the jaw (ONJ). Thus, ONJ in subjects who have been or are being treated with active BPs is generally referred to as Bisphosphonate Related Osteonecrosis of the Jaw (BRONJ).

As used herein, "active bisphosphonates (active BPs)" refer to bisphosphonates that exhibit potent antiresorptive activity and are used in antiresorptive therapies. As used herein "bisphosphonates" generally refer to compounds that have two phosphonate groups covalently linked to a carbon. Active bisphosphonates include "active nitrogen-containing bisphosphonates (active N-BPs)", which refers to bisphosphonates that have a chemical structure containing a nitrogen that forms hydrogen bonds with Thr201 and the carbonyl of Lys200 of human farnesyl diphosphate synthase (FPPS). Examples of active N-BPs include alendronate, ibandronate, minodronate, pamidronate, risedronate, and zoledronate.

As used herein, "inactive bisphosphonates (inactive BPs)" refer to bisphosphonates that are completely inactive as antiresorptive agents or partially inactive as antiresorptive agents as compared to active BPs that have been and/or are used in antiresorptive therapies. Partially inactive BPs are referred to herein as "low activity bisphosphonates (low activity BPs)". In other words, inactive BPs include low activity BPs. In some embodiments, inactive BPs have a chemical structure that lacks an α-hydroxy group. In some embodiments, inactive BPs have a chemical structure that has a pyridyl side chain that is para-substituted. In some embodiments, inactive BPs lack an α-hydroxy group and have a pyridyl side chain that is para-substituted. In some embodiments, the one or more inactive BPs has the following structure:

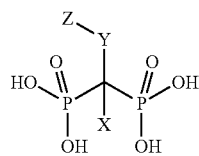

wherein X is H, hydroxyl, amino, halo, alkyl, or aryl; Y is hydroxyl, amino, alkyl, aryl, or heterocycle; and Z is a detectable label, such as a fluorophore, that may be present or absent. In some embodiments, X is a hydroxyl or H and Y is a pyridyl group that is para-substituted. In some embodiments, Z is present. In some embodiments, Z is absent.

Inactive BPs, according to the present invention, exhibit binding affinities for hydroxyapatite (HAP). In some embodiments, inactive BPs exhibit a binding affinity for hydroxyapatite that is more than that of active BPs. In some embodiments, inactive BPs competitively inhibit the binding of active BPs to hydroxyapatite. In some embodiments, inactive BPs displace active BPs that are bound to hydroxyapatite when administered thereto. In some embodiments, inactive BPs exhibit a bone affinity that is the same, or substantially similar to active N-BPs and little to no anti-osteoclastic activity. In some embodiments, inactive BPs exhibit a bone affinity that is higher than active N-BPs and little or none of the anti-osteoclastic activity of the active N-BPs.

In some embodiments, an inactive BP may contain a nitrogen within its chemical structure so long as the inactive BP inhibits human farnesyl diphosphate synthase (FPPS) to a lesser degree than the active N—BP being displaced or replaced. In some embodiments, an inactive BP may contain a nitrogen within its chemical structure so long as the strength of any hydrogen bonds formed between the nitrogen with Thr201 and with the carbonyl of Lys200 of human farnesyl diphosphate synthase (FPPS) is less than that of the hydrogen bonds formed between the active N—BP being displaced or replaced and Thr201 and the carbonyl of Lys200 of FPPS. In some embodiments, an inactive BP may contain a nitrogen within its chemical structure so long as the nitrogen does not form hydrogen bonds with Thr201 and the carbonyl of Lys200 of human farnesyl diphosphate synthase (FPPS). Enzymatic binding activity assays and protein modeling methods in the art may be used to screen for bisphosphonates that do not have a nitrogen that forms hydrogen bonds with Thr201 and the carbonyl of Lys200 of human farnesyl diphosphate synthase (FPPS). See, e.g., Ebetino, et al. (2011) Bone 49(1): 20-33; and Kavanagh, et al. (2006) PNAS, 103(20): 7829-7834. In some embodiments, inactive BPs have an inhibitory $IC_{50}$ of human farnesyl diphosphate synthase (FPPS), as measured according to the procedure in Dunford, et al. (2008) J Medicinal Chemistry 51(7): 2187-2195, of more than 4.1 nM, preferably 10 nM or more, more preferably 100 nM or more, even more preferably 500 nM or more, and most preferably 1000 nM or more. In some embodiments, inactive BPs do not inhibit protein prenylation at concentrations below 100 µM, as measured according to the procedure in Sun, et al. (2016) Bioconjugate Chem 27(2): 329-340. In some embodiments, inactive BPs do not inhibit bone resorption in in vivo models of bone metabolism, such as the Schenk or growing rat model (Seitsema, et al. (1989) Drugs Exptl. Clin. Res. XV(9): 389-396) at concentrations below those of active BPs. Examples of inactive BPs include 2-(pyridin-4-yl) ethane-1,1-diyl bisphosphonic acid (p-PyrEBP), 1-hydroxy-2-(pyridin-4-yl)ethane-1,1-diylbisphosphonic acid (p-RIS), methylene bisphosphonate (MBP), methylene hydroxyl bisphosphonate (MHDP), etidronate (EHDP), clodronate, isclodronate, tiludronate, 2-hydroxy-2-phosphono-3-(pyridin-3-yl)propanoic acid (3-PEHPC), and 2-hydroxy-3-(imidazo[1,2-a]pyridin-3-yl)-2-phosphonopropanoic acid (3-IP-EHPC).

Figure 18B:
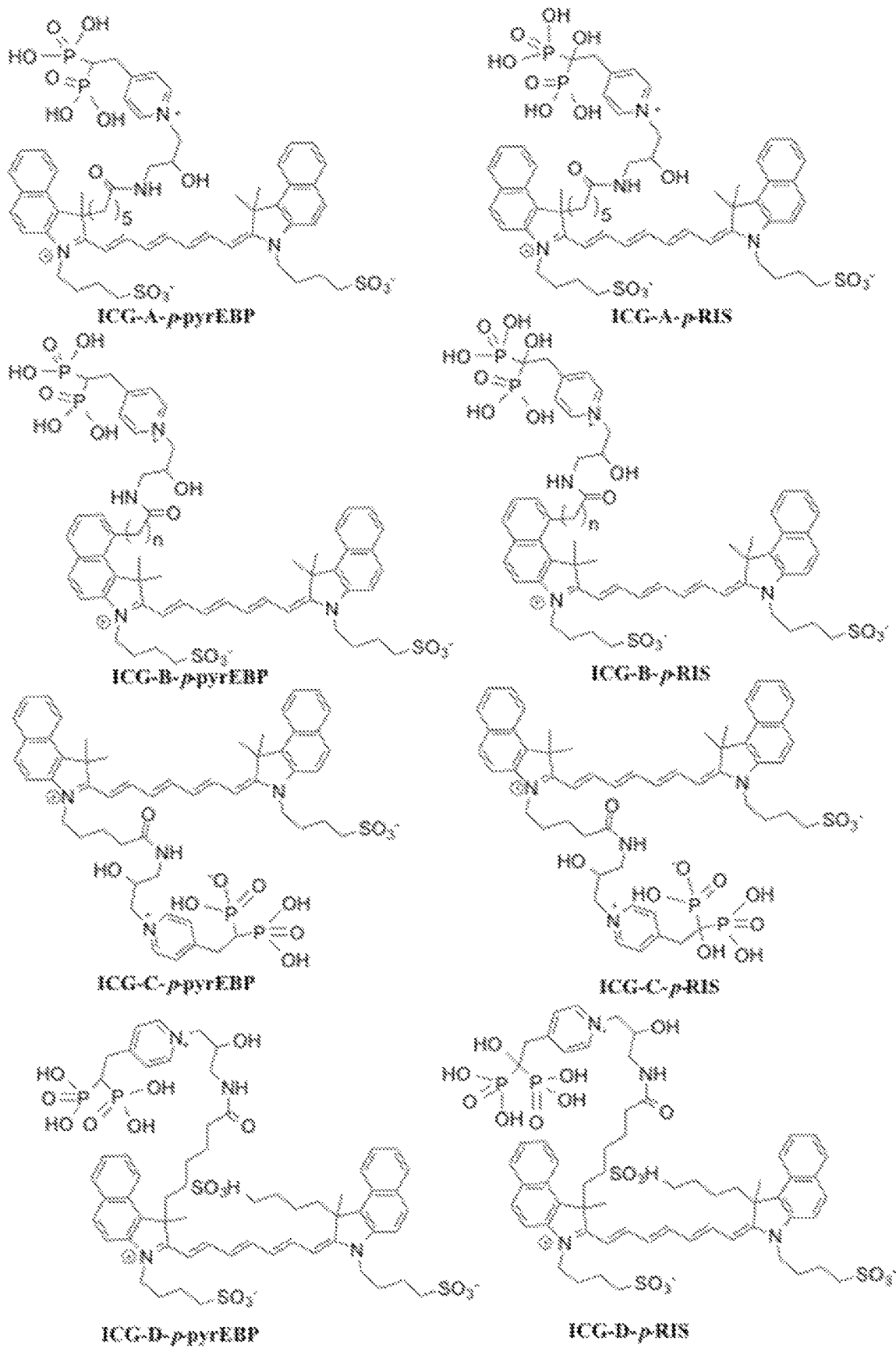
FIG. 18B presents the structures of several such ICG-BPs.

In some embodiments, inactive BPs have a detectable label, such as a fluorescent compound, attached thereto. In some embodiments, the inactive BPs comprise a bisphosphonate (which may be an active BP or an inactive BP) covalently attached to a fluorescent compound, such as ROX, FAM, AF647, ICG, Cy5, Sulfo-Cy5, Cy7, and IRDye 800CW. Examples of inactive BPs having a fluorescent compound conjugated thereto include compounds 7a1-7f2 of FIG. 2A to FIG. 2D, fluorescent p-PyrEBP conjugates such as those of FIG. 5A, fluorescent p-RIS conjugates such as those of FIG. 5B, the IGC compounds synthesized according to FIG. 18A1 to FIG. 18A4, and the IGC compounds set forth in FIG. 18B. In some embodiments, the inactive BPs that have a fluorescent compound conjugated thereto are 5-FAM-dRIS, 5(6)-FAM-dRIS, 5(6)-FAM-RIS, 5(6)-FAM-RISPC, 5(6)-RhR-RIS, 5(6)-RhR-dRIS, 5(6)-RhR-RISPC, 5(6)-ROX-RIS, 5(6)-ROX-RISPC, 5-FAM-RIS, 5-FAM-ZOL, 6-FAM-RIS, 800CW-ZOL, AF647-RIS, AF647-RISPC, AF647-ZOL, 800CW-RIS, 800CW-ZOL, 800CW-RISPC, ICG-RIS, ICG-ZOL, ICG-RISPC, and ICG-p-pyrEBP.

Inactive BPs also include pharmaceutically acceptable solvates, salts, and prodrugs of bisphosphonates, which are completely inactive as antiresorptive agents or partially inactive as antiresorptive agents as compared to active BPs that have been and/or are used in antiresorptive therapies. A "pharmaceutically acceptable solvate" refers to a solvate form of a specified compound that retains the biological activity, e.g., the anti-resorptive activity (or lack thereof), of the given compound. Examples of solvates include compounds of the invention in combination with water, isopropanol, ethanol, methanol, dimethyl sulfoxide, ethyl acetate, acetic acid, ethanolamine, or acetone. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Many organic compounds can exist in more than one crystalline form. For example, crystalline form may vary from solvate to solvate. Thus, all crystalline forms of inactive BPs and solvates thereof are within the scope of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

A "pharmaceutically acceptable prodrug" is a compound that may be converted under physiological conditions or by solvolysis to the specified compound or to a pharmaceutically acceptable salt of such compound. "A pharmaceutically active metabolite" refers to a pharmacologically active product produced through metabolism in the body of a specified compound or salt thereof. Prodrugs and active metabolites of a compound may be identified using techniques known in the art. See, e.g., Bertolini, G. et al., (1997) J. Med. Chem. 40:2011-2016; Shan, D. et al., J. Pharm. Sci., 86(7):765-767; Bagshawe K., (1995) Drug Dev. Res. 34:220-230; Bodor, N., (1984) Advances in Drug Res. 13:224-331; Bundgaard, H., Design of Prodrugs (Elsevier Press, 1985) and Larsen, I. K., Design and Application of Prodrugs, Drug Design and Development (Krogsgaard-Larsen et al., eds., Harwood Academic Publishers, 1991).

As disclosed herein, previously adsorbed active BPs in skeletal tissue, such as bone, can be displaced or removed by newly administered inactive BPs. Therefore, in some embodiments the present invention is directed to methods of removing or displacing bisphosphonates in skeletal tissue by administering one or more inactive BPs to the skeletal tissue. In some embodiments, the present invention is directed to methods of treating, inhibiting, or reducing BRONJ and/or bisphosphonate-related symptoms by administering to subjects in need thereof one or more inactive BPs. As used herein, "bisphosphonate-related symptoms" include symptoms, such as painful bone exposure and fistulation, abnormal skeletal fractures, etc., that are caused by or associated with treatment with an active BP. Examples of abnormal skeletal fractures in subjects who have been treated with active N-BPs include atypical femoral fractures and fractures of the hip. See, e.g., Paziana, et al. (2011) Bone 43: 103-110.

Locally administered inactive BPs are capable of binding to bone at the administration site without being distributed systematically in a significant concentration. In some embodiments, one or more inactive BPs are locally administered, e.g., injection into the bone tissue at the site where the active BP is to be displaced or removed, topical administration on the site of the bone tissue which is exposed during, for example, a surgical procedure, or application (e.g., injection) in the tissue adjacent to the site of the bone tissue to be treated in the form of a pharmaceutical formulation, e.g., on or in a drug delivery particle such as a liposome or nanovesicle, that reduces, inhibits, or prevents systemic distribution of the one or more inactive BPs. In some embodiments, the one or more inactive BPs are delivered in the form of nanovesicles. In some embodiments, the nanovesicles are nondeformable nanovesicles. In some embodiments, the nanovesicles are deformable nanovesicles. See, e.g., WO 2017/087685 and Subbiah, et al. (2017) J Drug Delivery, Article ID 4759839. In some embodiments, one or more inactive BPs are locally administered to subjects at the sites where BRONJ and/or bisphosphonate-related symptoms are likely to develop in who have been or are being treated with active BPs as a preventative measure against the development of BRONJ and/or bisphosphonate-related symptoms.

In some embodiments, the subjects to be treated are ones who are not candidates for a drug holiday. In some embodiments, the subject to be treated is one that suffers from osteoporosis or a bone related cancer or metastases (e.g., malignancy metastatic to bone or multiple myeloma) and being treated with an active BP. In some embodiments, where a subject is not a candidate for a drug holiday and is at risk for developing BRONJ and/or bisphosphonate-related symptoms as a result of being treated with an active N—BP, one or more inactive BPs may be applied locally to the site where the active N—BP is to be removed or displaced.

In embodiments where etidronate is administered to a subject as the inactive BP, etidronate is locally administered to the site where the active N—BP is to be displaced or removed. In some embodiments, etidronate is locally administered as a preventative measure against the development of BRONJ and/or bisphosphonate-related symptoms.

BRONJ Preventive/Therapeutic Modality: Disclosed herein is the first preventive and/or therapeutic procedure for BRONJ based on displacement of active BPs with inactive BPs. As disclosed herein, the administration of one or more inactive BPs likely results in a "competitive equilibrium"-based displacement of active BPs. In the context of BP adsorption to bone, "BP displacement" refers to the displacement of previously adsorbed BP with a subsequently administered BP. BP displacement has been demonstrated in vitro (FIG. 1) and in vivo (FIG. 10, FIG. 12A-FIG. 12C). As disclosed herein, BP displacement may be used as a preventive modality of BRONJ. For example, pre-adsorbed active BP may be effectively displaced by one or more inactive BPs that is administered systemically by, for example, intravenous or oral administration, or by local administration to a given treatment site (e.g., direct intraoral injection to the jaw or topical application to the oral mucosa).

Intraoral Approach: Local administration of one or more inactive BPs to the site of a dentoalveolar procedure such as a tooth extraction can displace one or more active BPs present in the bone, and thereby treat or reduce the risk of developing BRONJ. Importantly, intraoral application of one or more inactive BPs to the site of a dentoalveolar procedure, such as a tooth extraction can displace one or more active BPs present at the site and thereby reduce a subject's risk of developing BRONJ without significantly interfering with the therapeutic activity of active BPs in other tissues and/or at other sites within the subject. Thus, in some embodiments, a pre-adsorbed active BP may be effectively displaced or removed by intraoral injection of one or more inactive BPs to the jaw. In some embodiments, one or more inactive BPs may be administered in the form of a solution, gel or paste applied to the site to be treated. As an example of a treatment method according to the present invention, a subject may be administered an effective amount of one or more inactive BPs by intraoral application to the site of a dentoalveolar procedure, e.g., a tooth extraction, to treat or inhibit BRONJ and/or bisphosphonate-related symptoms or reduce the risk of the subject developing BRONJ and/or bisphosphonate-related symptoms. In some embodiments, one or more inactive BPs is applied to gingival/palatal tissue of a subject before, during, and/or after a dentoalveolar procedure.

Figure 3:
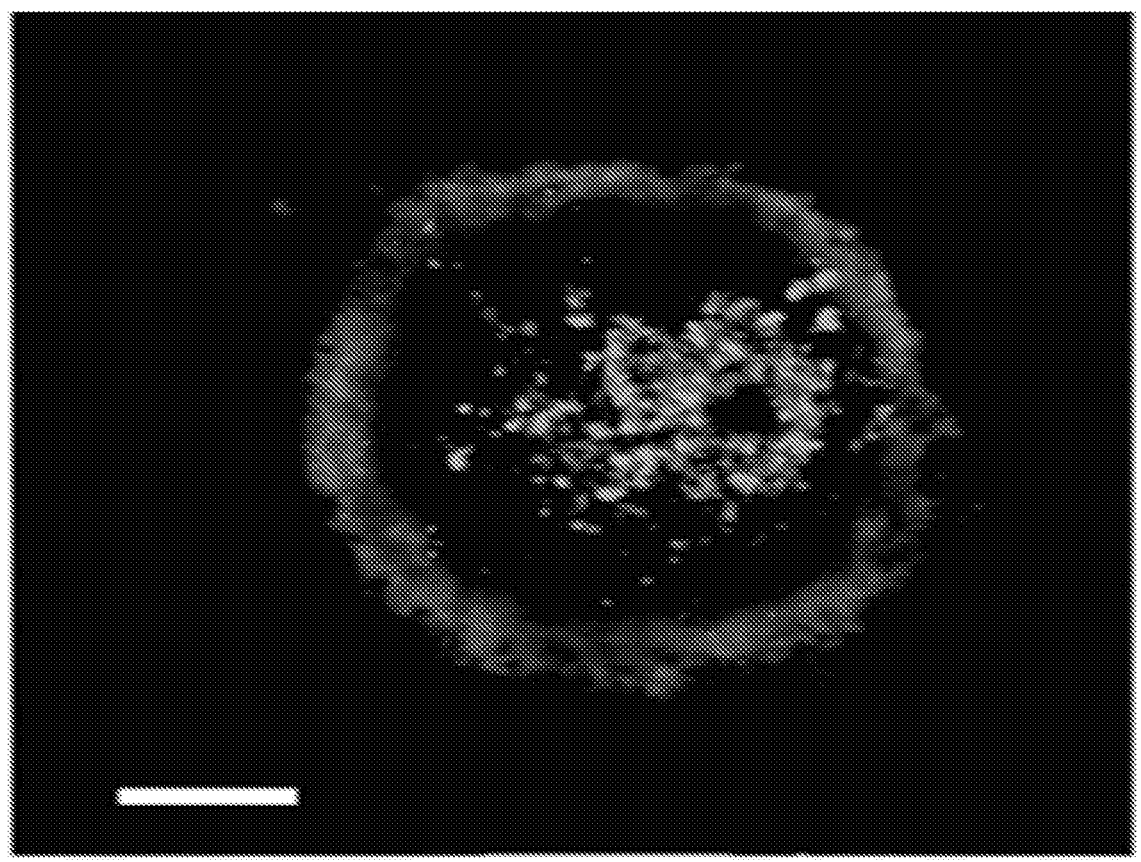
FIG. 3 are images of fluorescently labeled risedronate (RIS) adsorbed on dentine surface (green spots within circle in top image, and green spots and line underneath semi-circle in bottom image). An osteoclast (blue circle in top image and semi-circle in bottom image) adhering to the surface can be seen to ingest the released drug as it forms a local resorption pit (dashed white line). Upper image: 1 μm xy image 8 μm above the surface of the dentine; lower image: zx image of the same osteoclast.
Figure 3:
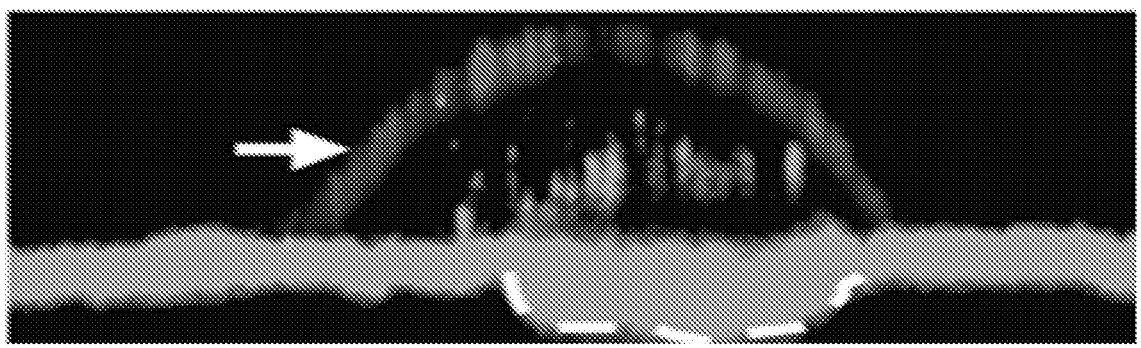

Fluorescently Labeled Bisphosphonates (FL-BP): Inactive BPs can be generated by conjugation of an active BP, such as RIS or ZOL and related analogues, with a detectable label, e.g., a fluorescent compound. Examples of suitable fluorescent compounds include fluorescein and derivatives thereof (including carboxyfluorescein (FAM), Carboxyl-X-Rhodamine (ROX), Alexa Fluor 647 (AF647), Rhodamine Red-X (RhR-X), IRDye 800CW (800CW), Sulfo-Cy5, indocyanine green (ICG), and analogues thereof, including those employed in the synthetic methods of FIG. 18A1 to FIG. 18A4, and those depicted in FIG. 18B. Examples of suitable FL-BPs are disclosed in FIG. 2A-FIG. 2D, FIG. 5A, FIG. 5B, FIG. 6, FIG. 18A1-FIG. 18A4, and FIG. 18B. FL-BPs may be used to monitor bisphosphonate localization and interactions in vivo, including by direct visualization of osteoclast incorporation of a bisphosphonate adsorbed onto the bone mineral surface (FIG. 3). FL-BPs, which are inactive BPs and include ICG-BPs, may be used to remove or displace active BPs in skeletal tissue as disclosed herein.

One or more inactive BPs with different mineral binding affinities, antiresorptive activities (ranging from inactive to partially active), and/or functions may be employed. For example, a series of different FL-BPs may be used to characterize the extent and amount of adsorbed in subjects, e.g., animal models, or monitor such treatments.

A feature of modern BPs such as RIS or ZOL is that their anti-resorptive effect depends on the structure of their nitrogen-containing substituent, distinct from their avid bone affinity, which is primarily due to the two phosphonate groups. In some embodiments, the inactive BPs according to the present invention have scaffolds that are based on N-containing bisphosphonates, e.g., risedronate (RIS) and zoledronate (ZOL), exhibit bone affinity that is the same or substantially similar to N-containing bisphosphonates yet exhibit little to no anti-osteoclastic activity. In some embodiments, the inactive BPs according to the present invention have scaffolds that lack an α-hydroxy group, a pyridyl group that is para-substituted (FIG. 4), or both, which will dramatically decrease antiresorptive activity without a significant impact on bone affinity as compared to the corresponding active BPs. In some embodiments, the inactive BPs according to the present invention comprise an active BP conjugated to a fluorescent compound, whereby conjugation to the fluorescent compound renders the bisphosphonate inactive or less active as an antiresorptive agent. These fluorescently labeled bisphosphonates (FL-BPs) are capable of being strongly adsorbed to the surface of hydroxyapatite, but substantially or entirely lack the anti-resorptive activity of the corresponding unconjugated bisphosphonate.

In some embodiments, the subject to be treated is an animal model. In some embodiments, the subject to be treated is a human. In some embodiments, the subject to be treated is at risk of developing BRONJ. In some embodiments, the subject to be treated has been treated with one or more active BPs.

In some embodiments, the present invention is directed to displacing a pre-adsorbed active BP drug in a bone of a subject which comprises administering one or more inactive BPs to the bone of the subject.

In some embodiments, the amount of one or more inactive BPs administered to the subject is a therapeutically effective amount or an effective amount. As used herein, an "effective amount" is a dose that results in an observable difference as compared to a placebo. In some embodiments, an effective amount of one or more inactive BPs is one that displaces more than 50% of an active BP in a tissue, such as bone, when administered thereto. A "therapeutically effective amount", refers to an amount of one or more compounds of the present invention that, when administered to a subject, (i) treats or inhibits a particular disease, condition, or disorder, (ii) attenuates, ameliorates, or eliminates one or more symptoms of the particular disease, condition, or disorder, and/or (iii) inhibits or delays the onset of one or more symptoms of the particular disease, condition, or disorder, as compared to a control. A therapeutically effective amount of one or more compounds of the present invention will vary depending upon factors such as the given compound(s), the pharmaceutical formulation, route of administration, the type of disease or disorder, the degree of the disease or disorder, and the identity of the subject being treated, but can nevertheless be readily determined by one skilled in the art. For example, a "therapeutically effective amount" of one or more inactive BPs is one that treats, inhibits, prevents, or reduces a sign or symptom of BRONJ as compared to a negative control. Therapeutically effective amounts may be determined from animal models. For example, a therapeutically effective amount for a human can be formulated based on amounts that have been found to be therapeutically effective in animal models.

In some embodiments, a therapeutically effective amount of the one or more inactive BPs are administered as a single dose of about 5-20, about 10-15, or about 11-12 milligrams per kilogram weight of the subject prior to, during, or after an event, such as a dentoalveolar procedure, tooth extraction, implant procedures, the establishment of periodontitis, and the like. In some embodiments, the one or more inactive BPs are administered during or immediately after the event. The skilled artisan will appreciate that certain factors may influence the dosage required to effectively treat a subject, including but not limited to the severity of the disease or disorder, previous treatments, the general health and/or age of the subject, and other diseases present.

In some embodiments, the present invention is directed to a composition comprising, consisting essentially of, or consisting of one or more inactive BPs. Compositions of the present invention, including pharmaceutical compositions, comprise one or more inactive BPs and a pharmaceutically acceptable carrier. As used herein, the terms "pharmaceutical composition" and "pharmaceutical formulation" are used interchangeably to refer to a composition suitable for pharmaceutical use in a subject. A pharmaceutical composition generally comprises an active agent, e.g., one or more inactive BPs and a pharmaceutically acceptable carrier, e.g., a buffer, adjuvant, diluent, and the like.

The one or more inactive BPs to be administered to a subject may be provided as a pharmaceutical formulation. Pharmaceutical formulations may be prepared in a unit-dosage form appropriate for the desired mode of administration. The pharmaceutical formulations of the present invention may be administered by any suitable route including oral, rectal, nasal, topical (including buccal and sublingual), vaginal, mucosal, and parenteral (including subcutaneous, intramuscular, intravenous, and intradermal). It will be appreciated that the route of administration may vary with the condition and age of the recipient, the nature of the condition to be treated, and the given compound(s) of the present invention. In some embodiments, the route of administration is oral. In some embodiments, the route of administration is mucosal. In some embodiments, the one or more inactive BPs are delivered to the oral mucosa of a subject. In some embodiments, a pharmaceutical formulation according to the present invention is an aqueous solution of the one or more inactive BPs. In some embodiments, a pharmaceutical formulation according to the present invention is a suspension, e.g., in a lipophilic gel, comprising one or more inactive BPs. In some embodiments, a pharmaceutical formulation according to the present invention is a liposomal or nanovesicle preparation comprising one or more inactive BPs encapsulated in the liposomes or nanovesicles. In some embodiments, the nanovesicles are nondeformable nanovesicles. In some embodiments, the nanovesicles are deformable nanovesicles. See, e.g., WO 2017/087685 and Subbiah, et al. (2017) J Drug Delivery, Article ID 4759839. In some embodiments, a pharmaceutical formulation according to the present invention is a trans-oral mucosal gel formulation comprising one or more inactive BPs. In some embodiments, a pharmaceutical formulation according to the present invention is an oro-dental mucoadhesive proniosomal gel formulation comprising one or more inactive BPs.

It will be appreciated that the actual dosages of the inactive BPs used in the pharmaceutical formulations will vary according to the particular compound(s) being used, the particular composition formulated, the mode of administration, and the particular site, subject, and disease being treated. Optimal dosages for a given set of conditions may be ascertained by those skilled in the art using dosage determination tests in view of the experimental data for a given compound. Administration of prodrugs may be dosed at weight levels that are chemically equivalent to the weight levels of the fully active forms.

Pharmaceutical compositions and formulations according to the present invention comprise a therapeutically effective amount of one or more inactive BPs and a pharmaceutically acceptable carrier. As used herein, "pharmaceutically acceptable vehicle" and "pharmaceutically acceptable carrier" are used interchangeably and refer to and include any and all solvents, dispersion media, coatings, antibacterial and antifungal agents, isotonic and absorption delaying agents, excipients, diluents, and the like, that are compatible with pharmaceutical administration and comply with applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., Remington: The Science and Practice of Pharmacy. $20^{th}$ ed. (2000) Lippincott Williams & Wilkins. Baltimore, Md., which is herein incorporated by reference. The pharmaceutically acceptable carrier employed may be either a solid or liquid. Exemplary of solid carriers are lactose, sucrose, talc, gelatin, agar, pectin, acacia, magnesium stearate, stearic acid, and the like. Exemplary of liquid carriers are syrup, peanut oil, olive oil, pharmaceutical grade water, and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate, and the like. In some embodiments, the pharmaceutically acceptable carrier is a liposome. In some embodiments, the pharmaceutically acceptable carrier is a nanovesicle, which may be deformable or nondeformable. In some embodiments, the pharmaceutically acceptable carrier is a proniosome.

Toxicity and therapeutic efficacy of inactive BPs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side-effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, a therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are intended to illustrate but not to limit the invention.

Animals

Mouse Osteonecrosis of the Jaw (ONJ) Model

The C57BL/6J (B6) mice model of ONJ is used. The consistent tissue source in this study is mouse maxillary bone with or without tooth extraction, as well as femurs, mandibles and L4/L5 lumber bones. Tooth extraction animal models for studying wound healing in mice have been well established in our and other laboratories. Systemic bisphosphonate treatment is accomplished by IV injection and the proposed local application of FL-BP is accomplished by intraoral injection to gingival/palatal tissue of mouse maxilla. Mice are subjected to maxillary molar extraction. After anesthesia and vital signs checked, the animal is placed on a bed supporting the isoflurane tubing while keeping the mouth opening. Ophthalmic ointment (bland, e.g., Lacrilube) is applied. The maxillary molar area is wiped with 0.12% Chlorhexidine gluconate solution (Peridex, oral rinse). An autoclaved dental explorer is used as an exodontia elevator after careful reflection of the cervical mucosa to minimize post-extraction discomfort. An autoclaved cotton swab is placed on the extraction socket until the initial blood coagulation is established. Maxillary 1st molar is then extracted unilaterally from so that the remaining untreated side can be utilized for chewing. In our previous experiments, the entire procedure takes about 5-15 minutes.

ONJ occurs in the oral cavity. Dental procedures (commonly tooth extraction) have been noted as a trigger for the onset of bisphosphonate-associated ONJ. It is necessary to use animals to perform the proposed research because there are no appropriate alternative models of oral wound healing. It would be impossible to study the biology and molecular mechanism of wound healing if other models are used. Extrapolation of the future wound healing treatment to the human patients would be impossible without using animals. Mice are used because their similarity in wound healing process to humans; and the immediate availability of genetically modified strains that are directly relevant to our hypothesis. The estimated number of animals required for this study is based on the consideration that a comprehensive study of bisphosphonate treatment on wound healing will be achieved.

Veterinary care is provided through the Department of Laboratory Animal Medicine at UCLA Medical Center. Animal subjects are examined following surgery; veterinary consultation is obtained for complications such as infection. No animals are used which shows signs of respiratory disease or distress, or enteric disease. UCLA is fully accredited the American Association of Accreditation of Laboratory Animal Care (AAALAC).

To prevent any distress, discomfort, or pain to any of the animals, procedures are performed under general anesthesia, using isoflurane inhalation (1-2%). After the survival surgery, the animal is placed on a water-circulating heating pad. The animal is monitored for cardiovascular and respiratory function and attended continuously until the animal forms a sternal position. To prevent post-procedural discomfort, analgesics are administered. Whereas no special treatments are considered for the husbandry of these mutant mice, any possible infections are monitored.

Animals are euthanized at the completion of experiments. Euthanasia is completed by 100% carbon dioxide inhalation. The method is consistent with the recommendations of the Panel of Euthanasia of the American Veterinary Medical Association.

Example 1

Synthesis and Characterization of FL-BPs with Variable Mineral Binding Affinities Bisphosphonates having a fluorescent compound conjugated thereto (FL-BPs) that have low or undetectable biological activity but possess high bone mineral affinity were synthesized. Different fluorophores were conjugated to bisphosphonates using "Magic linker" technology (see, e.g., U.S. Pat. No. 8,431,714). In vitro characterization of binding affinity/pharmacological activity was performed.

Experiment 1-1: Synthesis of FL-BPs

Figure 5A:
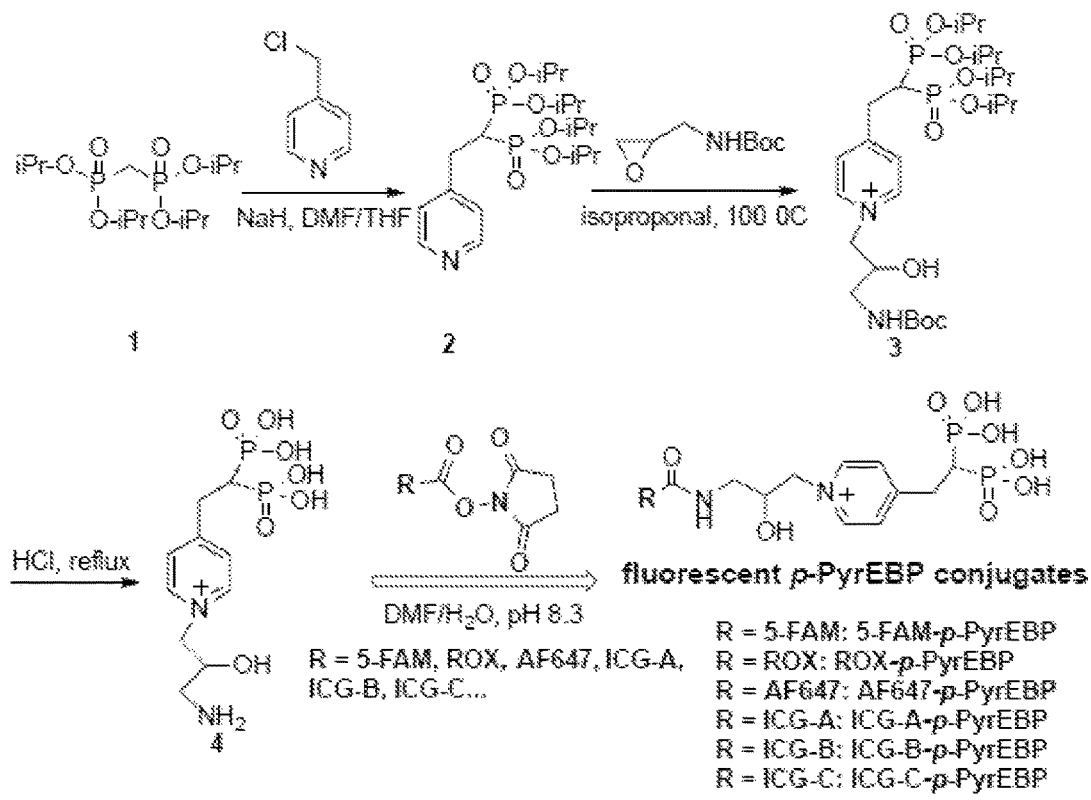
FIG. 5A and FIG. 5B schematically show the synthesis of some FL-BPs.
Figure 6:
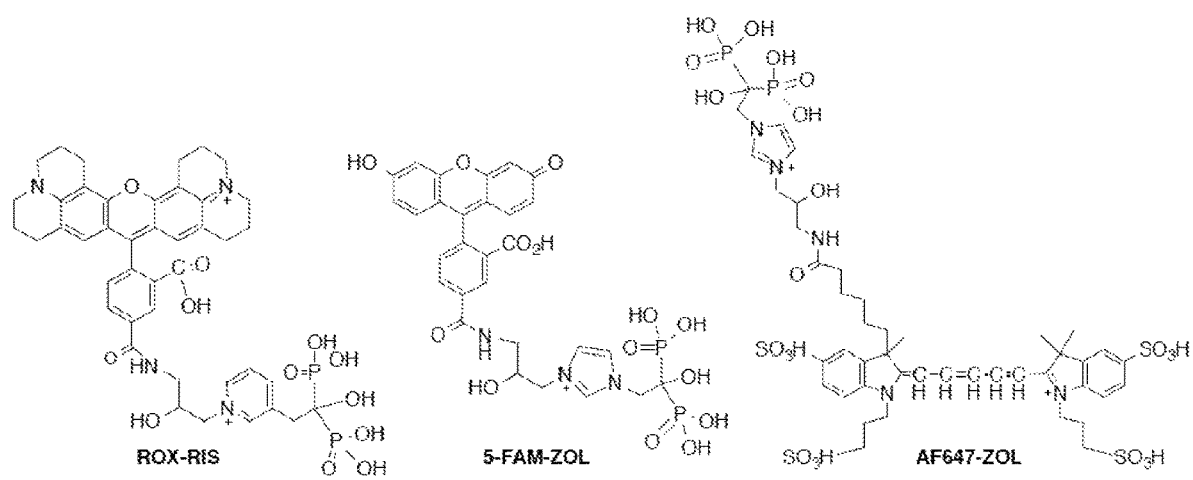
FIG. 6 shows the structural formulas of several FL-BPs.

FL-BPs were synthesized using "Magic linker" technology (see, e.g., U.S. Pat. No. 8,431,714) to conjugate BP compounds, e.g., RIS, ZOL, and other related analogues (e.g., FIG. 4) to fluorophores as schematically shown in FIG. 5A. The conjugates, FL-BPs, were obtained in 50-77% yield (>98% purity) and were characterized by UV-VIS, fluorescence emission, 1H NMR, 31P NMR, and HRMS. FIG. 6 shows the structural formulas of three FL-BPs that were synthesized. In some embodiments, BPs used according to the present invention are those as set forth in U.S. Pat. No. 8,431,714, which is herein incorporated by reference in its entirety. An example of an low activity BP is 1-hydroxy-2-(pyridin-4-yl)ethane-1,1-diyl bisphosphonic acid (p-RIS); another example of an inactive BP is 2-(pyridin-4-yl)ethane-1,1-diyl bisphosphonic acid (p-PyrEBP).

Experiment 1-2: In Vitro Characterization of FL-BPs

A) Mineral Binding Affinity Assay

Hydroxyapatite assays indicate that the FL-BPs generally retain substantial affinity for bone mineral that reflect the affinity of the BP component and to a lesser extent, the affinity of the conjugated fluorophore. Hydroxyapatite (Macro-Prep® Ceramic hydroxyapatite Type II 20 µM) was obtained from Bio-Rad Laboratories, Inc. Hercules, Calif. Accurately weighed hydroxyapatite powder (1.4-1.6 mg) was suspended in a 4 mL clear vial containing the appropriate volume of assay buffer (0.05% (wt/vol) Tween20, 10 µM EDTA and 100 mM HEPES pH=7.4) for 3 hours. Hydroxyapatite was then incubated with increasing amounts of FAM-BP and ROX-BP (0, 25, 50, 100, 200, and 300 µM). Samples were gently shaken for 3 hours at 37° C. in appropriate volume of assay buffer (0.05% (wt/vol) Tween20, 10 µM EDTA and 100 mM HEPES pH=7.4). Subsequent to the equilibrium period, the vials were centrifuged at 10,000 rpm for 5 minutes to separate the solids and the supernatant. 0.3 mL of the supernatant was collected and the equilibrium solution concentration is measured by using Shimadzu UV-VIS spectrometer. For the calibration series, FL-BP probe standards were prepared by serial dilution from the stock solution with the same isotherm buffer to give the range from 0 to 400 µM. Calibration curves were constructed using standard solutions of the target FL-BPs. Fluorescent emission can also be used to calculate the binding parameters. Nonspecific binding was measured with a similar procedure in the absence of hydroxyapatite as control. Binding parameters (Kd and Bmax, represent the equilibrium dissociate constant and maximum number of binding sites, respectively) were calculated using the PRISM program (Graphpad, USA). The binding parameters of each compound was measured in 5 independent experiments. The compounds with equilibrium dissociation constant (Kd) higher than about 100 µM (about 10× of Kd of parent BPs) were eliminated from further investigation. A two-sample t-test was used to evaluate the binding parameters of the probes. The sample size (n=5) in each group was able to detect the effect size 1.72 for this hypothesis at a power of 80% and a one-side Type I error of 0.05.

Figure 7:
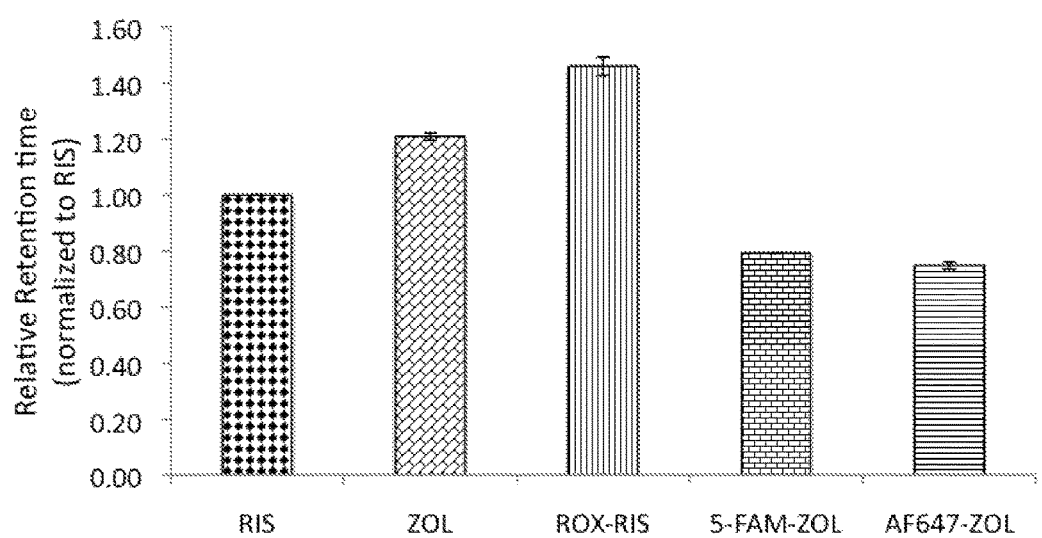
FIG. 7 is a bar graph showing hydroxyapatite (HAP) binding affinity of Zoledronate (ZOL), ROX-RIS, 5-FAM-ZOL, and AF647-ZOL. Relative retention times were normalized to RIS.
Figure 8A:
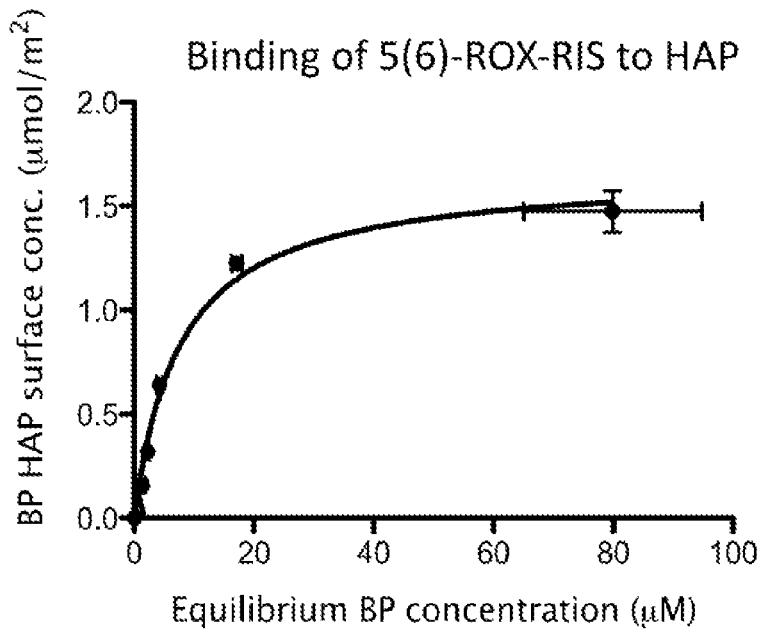
FIG. 8A to FIG. 8D show adsorption isotherms for binding of four FL-BPs to hydroxyapatite (HAP) at pH 6.8 (top graphs) with Scatchard plots of the same data (bottom graphs), data are mean±SD (n=3).
Figure 8A:
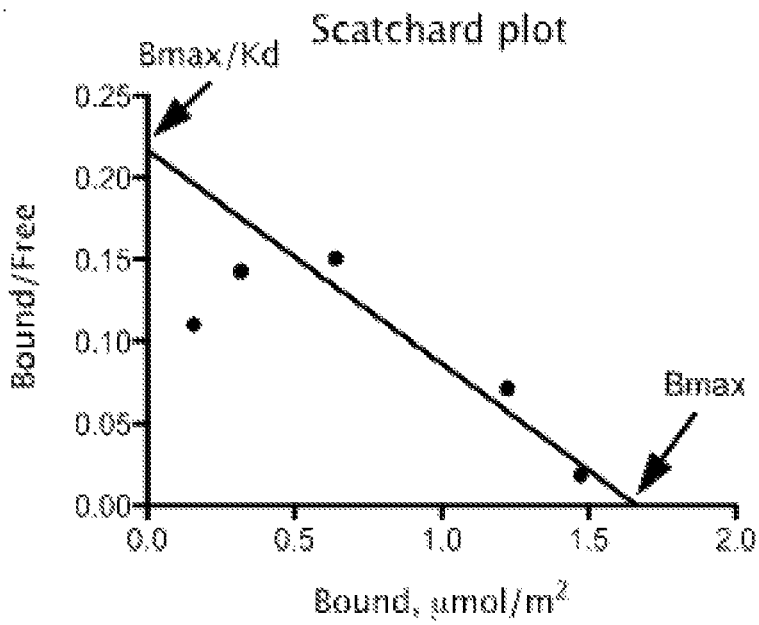
Figure 8B:
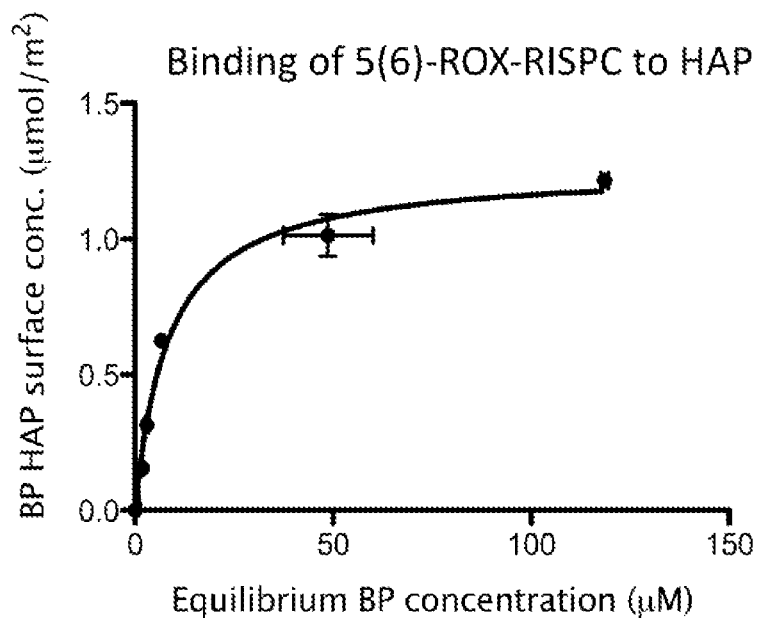
Figure 8B:
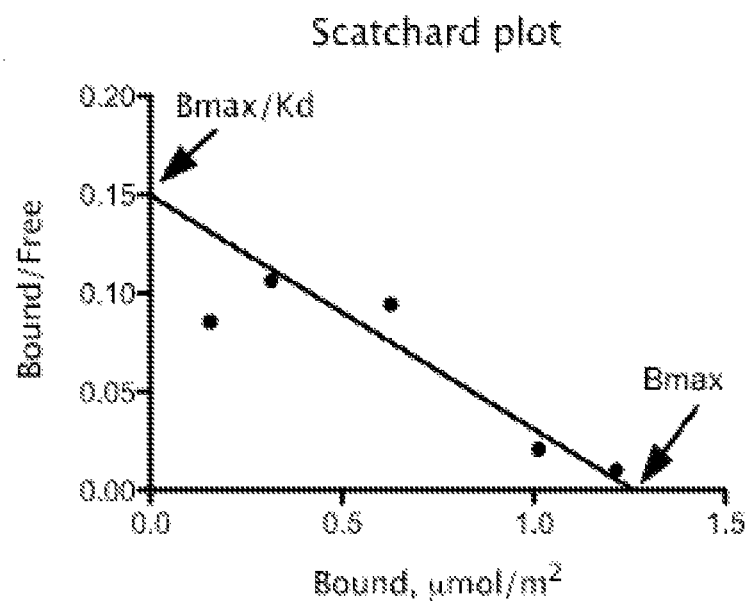
Figure 8C:
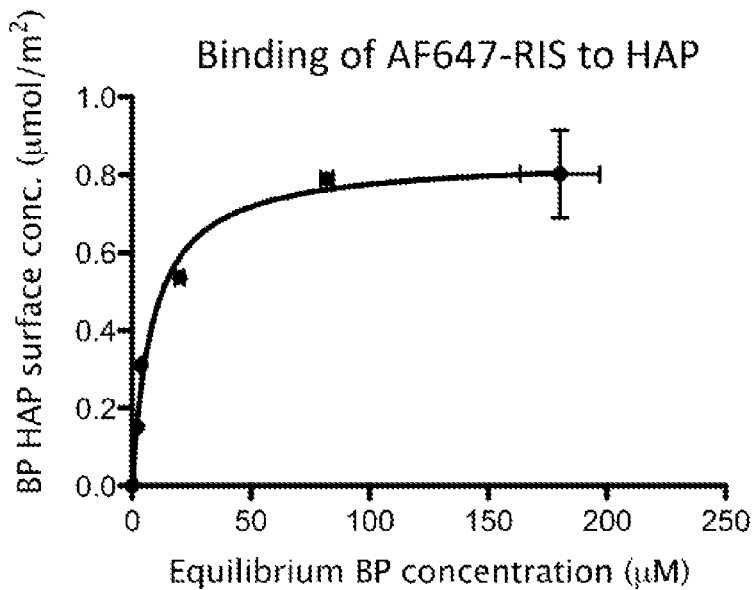
Figure 8C:
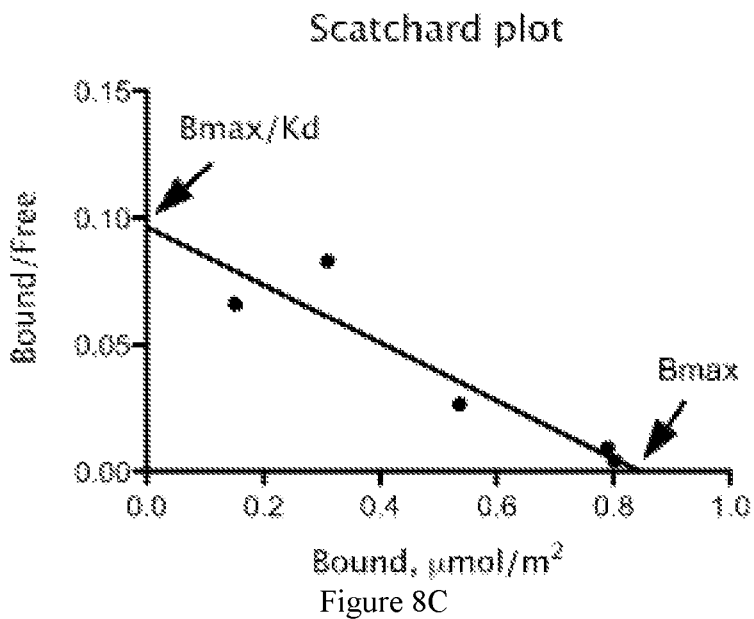
Figure 8D:
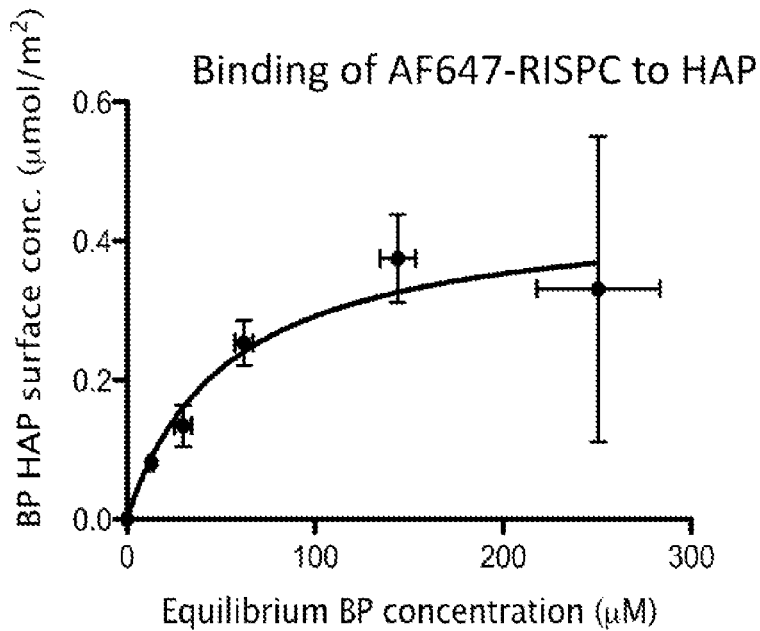
Figure 8D:
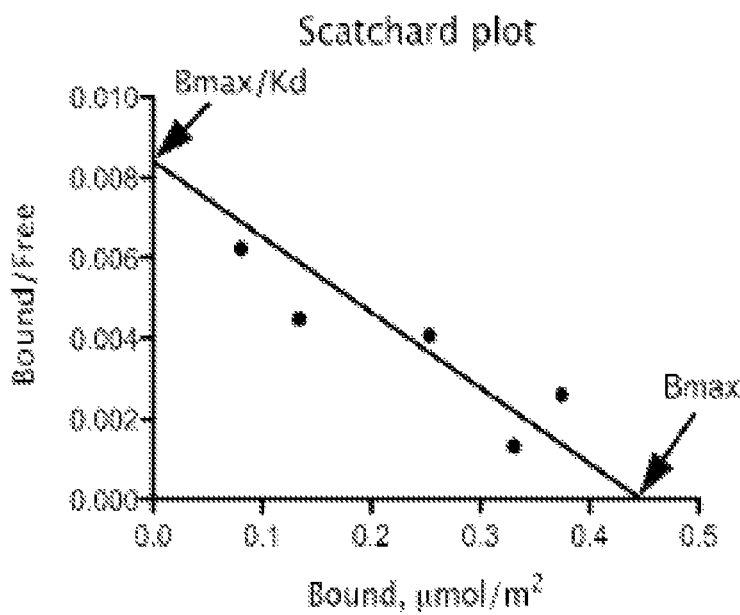

Hydroxyapatite assays confirm that the FL-BPs generally retain substantial bone mineral affinity. The fluorophore component does exert some influence on affinity: 5-FAM-ZOL and AF647-ZOL showed a small reduction, while ROX-RIS showed an enhancement (FIG. 7). Thus, the bone affinity of bisphosphonates is substantially retained when conjugated to different fluorophores.

A method based on Langmuir adsorption isotherms was used to measure binding affinity measurement of representative fluorescent BP probes; the results are in good agreement with results from the hydroxyapatite column assay (FIG. 8A-FIG. 8D).

B) Biological Activity In Vitro Assay

In vitro activity assays were performed by using bone marrow macrophages and culturing them with M-CSF on bovine bone slices for 2 days to enrich for osteoclast precursors (OCPs) and then treating with RANKL for a further 3 days to develop and isolate multinucleated osteoclasts. Bone slices were pre-adsorbed with FL-BPs and serially diluted numbers of OCPs were cultured on them. Resorption pit areas were measured. Separately, osteoclasts were collected and total protein samples were prepared. The prenylation of Rap1a were examined by Western blot. Each experimental group (n=5) will be compared with the control (n=5) in the prototype experiment. Experiment 1-2-B has the same power calculation as Experiment 1-2-A.

In a preliminary study, to determine the effect of fluorescent ZOL analogues on cell viability, J774.2 mouse macrophages were plated at $2\times10^5$ cells/ml in 96-well plates and left to adhere overnight. Cells were then treated with 10, 100, or 500 µM of fluorescent ZOL analogues, ZOL, or vehicle, for 48 hours at the end of the incubation period, the medium was removed, and cells were washed twice with PBS. Medium with AlamarBlue reagent was then added and cells are incubated for a further 3 hours. Western blot and cell viability assays indicated a significant biological effect of the FAM conjugates. These results demonstrate that 5-fluorescein-ZOL conjugates (and similar RIS conjugates) retain observable antiprenylation and the anti-resorptive properties of the parent BP drug.

Alternative Approaches

Although most of the in vitro systems and assays are well established for fluorescent BP probes, hydroxyapatite column assays may be used for binding affinity assays. Dentine discs may also be used instead of bovine bone slices. The methodology can be applied to generate other FL-BPs with appropriate modifications on the structure of BP molecules, such as p-RIS, to obtain the desired affinity.

Example 2

Oral Application of FL-BP for Local Adsorption to Jawbone and Competitive Displacement of Pre Adsorbed FL-BP Via IV Injection This experiment was carried out to demonstrate BP displacement in vivo. Pre-adsorbed FL-BP in mice resulting from systemic administration via tail vain injection is challenged by a local application to gingival/palatal tissue of maxilla using a FL-BP carrying different fluorophore. Local application may include: a) injection to gingival/palatal tissue; b) mouth wash; and c) topical application for transmucosal delivery. FL-BP may be applied to the periosteal space of jawbone. The dose and the time point of oral injection is established by quantitative fluorescence imaging analysis to achieve maximum displacement efficiency. Consideration was also given to possible distant toxic effects. Femurs, mandibles, and L4/L5 lumber bones were examined.

Experiment 2-1

This experiment establishes the oral injection protocol and determines the relationship between injection doses and maxillary bone adsorption fluorescent signal. A total of 30 female B6 mice are divided in 5 groups (n=6). In each group, a single intraoral injection of 0, 1, 5, 10, or 50 µM of ROX-BP in 25 µl of 0.9% NaCl solution were performed to the gingival/palatal tissue. One week after the oral injection, skull (containing the maxillary injection site), mandible, femur, and L4/L5 lumber bones were harvested and soft tissues were removed. Bone specimens kept in PBS were evaluated by the standardized fluorescent biophotonics and the signal was quantified using the proprietary program (LAS3000, FUJIFILM).

Experimental Results

Figure 9:
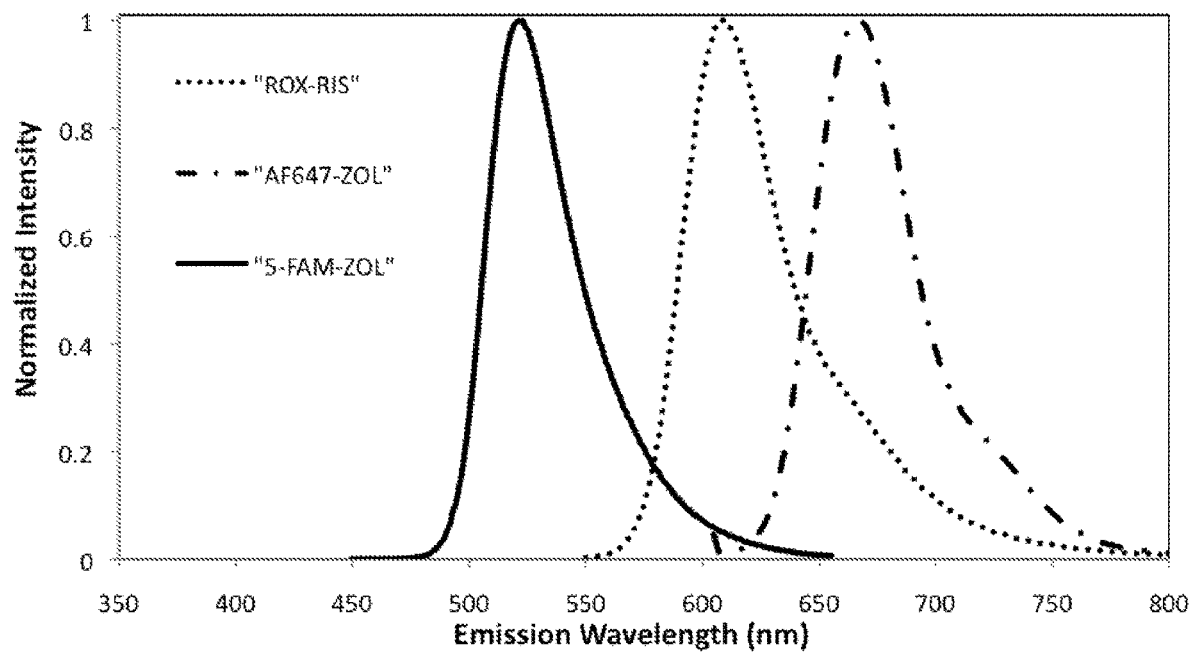
FIG. 9 shows emission wavelengths of 3 different FL-BPs (ROX-RIS, AF647-ZOL and 5-FAM-ZOL). From left to right, the curves are 5-FAM-ZOL, ROX-RIS, and AF647-ZOL. Overlap between 5-FAM and AF647 is minimal.

As shown in FIG. 9, ROX and FAM have overlapping emission spectra resulting in suboptimal fluorescent signal separation (data not shown). Therefore, AF647-ZOL was selected as the candidate FL-BP to test displacement of FAM-ZOL and vice versa. Use of complementary fluorescent signals from the original and displacing labeled BP permitted the original BP loading and its response to the displacing BP loading to be monitored.

The mouse intra-oral injection protocol was established by using a Hamilton syringe with a 33-gauge needle. Under a surgical microscope, 2 µl solution was injected to the palatal gingiva of left first molar of mouse maxilla. After slow injection, the needle was left in the tissue for 3 minutes and then gently removed.

Using this method, 2 µl of 0 µM, 0.5 µM or 5.0 µM AF647-ZOL was injected to mouse maxillary oral mucosa to mice 6 days after retro-orbital IV injection of 100 µl of 50 µM FAM-ZOL. Mouse tissues were harvested 1 day after oral injection and maxillary bones were subjected to standardized fluorescent biophotonics image obtained using an excitation wavelength of 460 nm and a 515 nm filter (LAS3000, FUJIFILM Corp).

Figure 10:
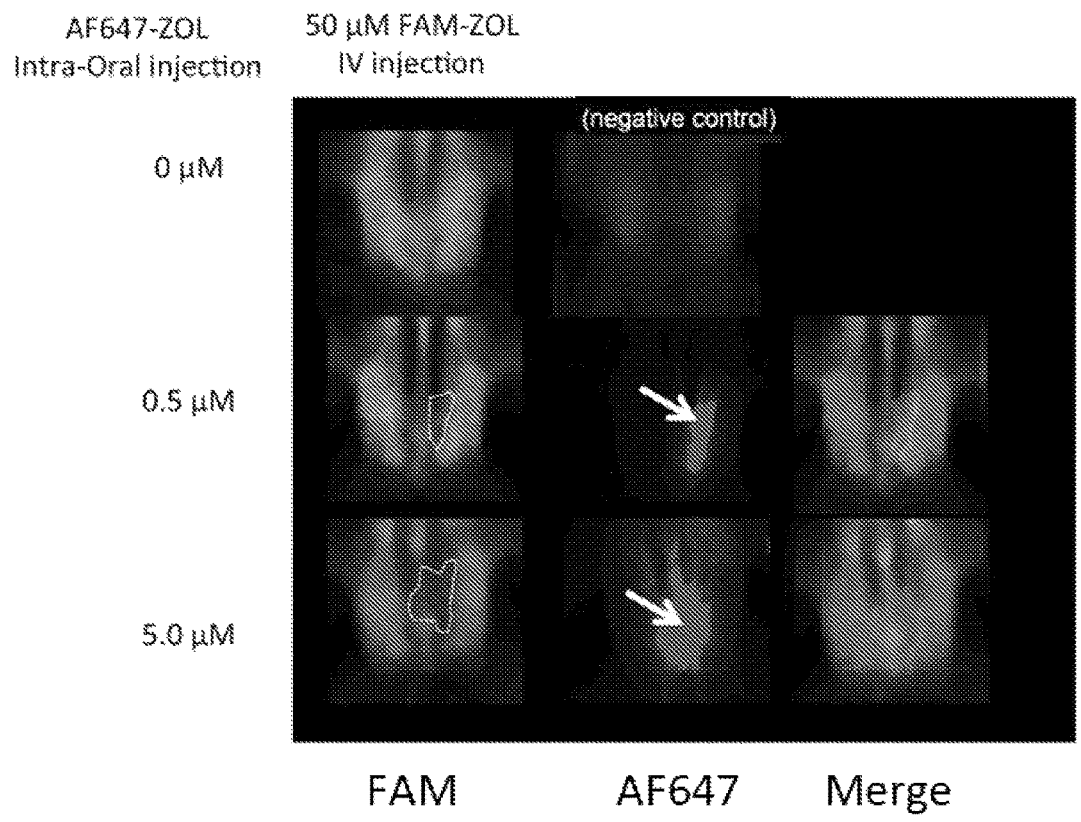
FIG. 10 are representative images of mice maxilla. AF647-ZOL was orally injected into maxilla of mice pre-injected with 5-FAM-ZOL. A dose dependent adsorption of AF647-ZOL was observed at and around the injection site (arrow). Reduction of FAM-ZOL signal was observed qualitatively (dotted line). Fluorescent imaging of the femur showed that, unlike intravenous administration, intra-oral injection of AF647-ZOL did not result in systemic distribution to the distant skeletal system.

As shown in FIG. 10, this method consistently and successfully delivered FL-BP to mouse maxillary oral mucosa tissue. AF647-ZOL intra-oral injection gave rise to a dose dependent AF647 signal at and around the injection site on the palatal bone. Furthermore, there was an indication that pre-adsorbed FAM-ZOL was removed by the AF647-ZOL. However, the quantitative evaluation of this displacement presented some difficulty, largely due to the complex anatomy of mouse maxilla.

Experiment 2-2

This experiment examines the postulated BP displacement at the intraoral injection site. A total of 30 female mice were divided into 5 groups (n=6). All groups received a single IV injection of 200 µl of 350 µM FAM-BP. One week later, mice in each group received an intraoral injection of 25 µl of 0, 1, 5, 10, or 50 µM ROX-BP to gingival/palatal tissue. Mice were euthanized 1 week after the intraoral injection and skull, mandible, femur and L4/L5 lumber bone were harvested. The bone specimens were evaluated for 2 color fluorescent biophotonics and each signal was quantified.

Figure 11:
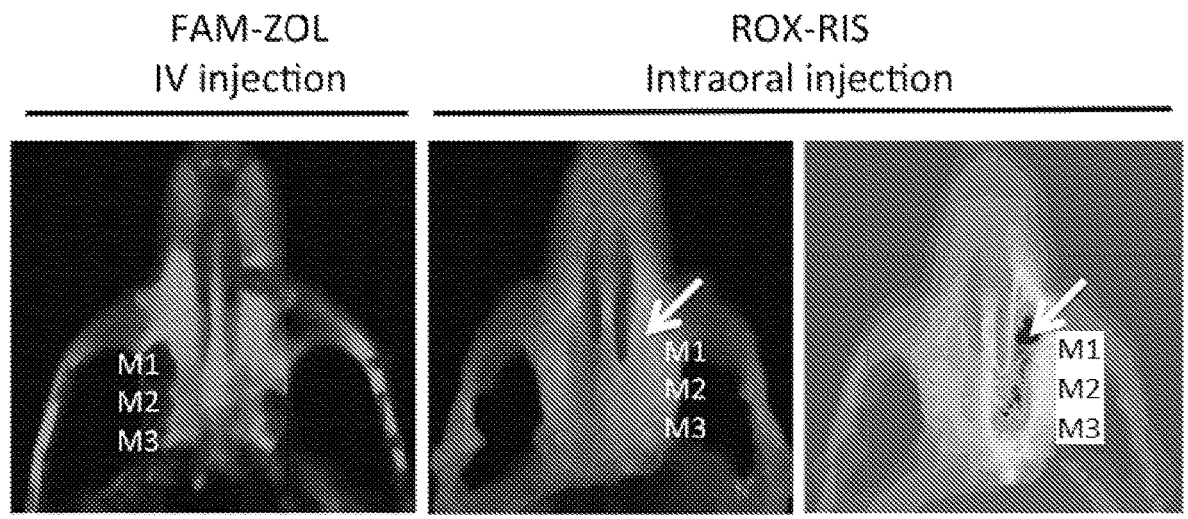
FIG. 11 shows fluorescent biophotonic images of mouse maxilla after 5-FAM-ZOL IV injection (left panel) or ROX-RIS intraoral injection (center and right panels).

In a preliminary study female C57B16/J (B6) mice (8 weeks old) received either a single IV injection via tail vein of 200 µl of 350 µM 5-FAM-ZOL (5-FAM-ZOL, # BV111001, BioVinc LLC, Culver City, Calif.) or a single intraoral injection of 25 µl of 50 µM ROX-RIS (5(6)-ROX-RIS, # BV150101, BioVinc LLC, CA) to gingival/palatal tissue at maxillary left first molar (white arrow in FIG. 11). One week later, mice were euthanized 3 weeks after the IV injection of 5-FAM-ZOL or 2 days after the intraoral injection of ROX-RIS. Skulls (containing maxilla) were harvested and standardized fluorescent biophotonics image was obtained using an excitation wavelength of 460 nm and the 515 nm filter (LAS3000, FUJIFILM Corp). Strong and relatively uniform green fluorescent signal was detected throughout the maxilla and zygomatic arch after the IV injection of FAM-ZOL. By contrast, the palatal bone around the intraoral injection site of ROX-RIS showed a localized red fluorescent signal (FIG. 11).

Experimental Results

Mice were pre-treated by 100 µl of 50 µM AF647-ZOL retro-orbital IV injection. Six days later, mice received sub-periosteal injection to cranial bone with 10 µl of 0 µM, 1 µM, 10 µM, or 50 µM FAM-ZOL. The cranial bone was harvested and soft tissues were removed. The fluorescent signals of AF647 and FAM were measured by standardized fluorescent biophotonics. The cranial bones were then prepared for cryosection. Cross-sections were made by the tape method and evaluated by confocal laser scanning microscopy.

Figure 12A:
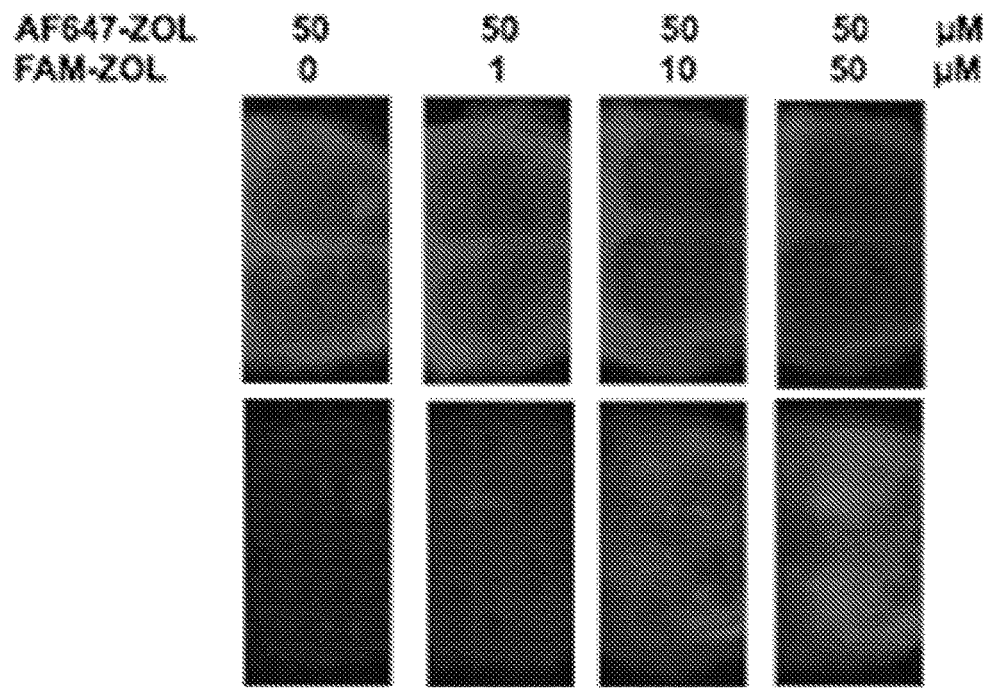
FIG. 12A to FIG. 12C show the displacement and replacement of AF647-ZOL and 5-FAM-ZOL.
Figure 12B:
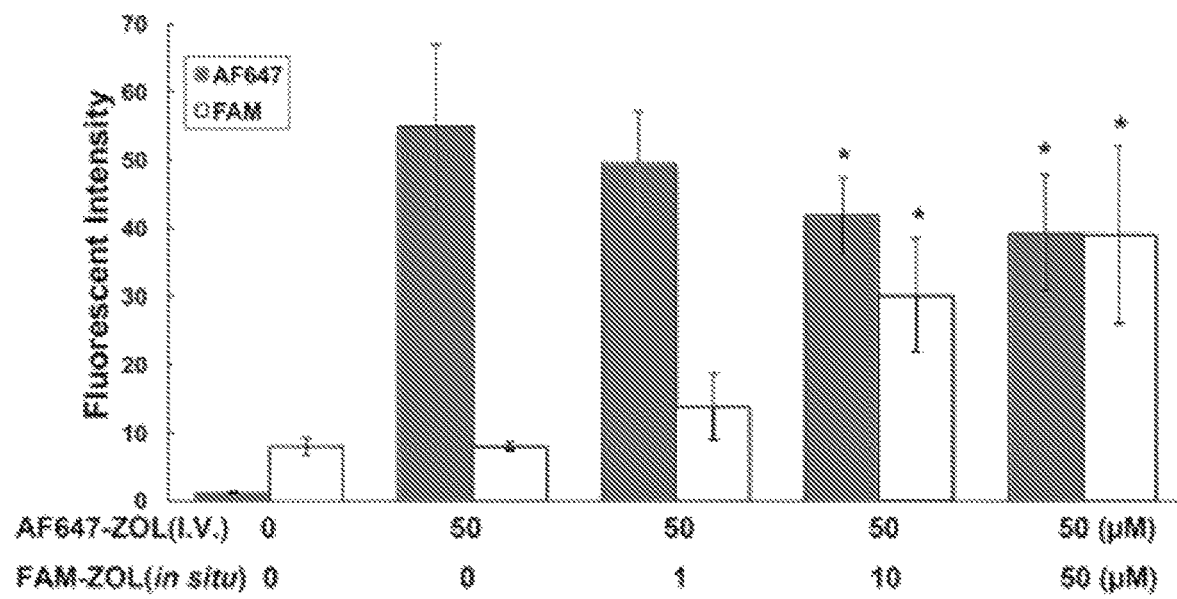

The FAM signal of sub-periosteally injected FAM-ZOL showed a dose dependent increase on the cranial bone at the injection site. As shown in FIG. 12A, AF647 signal at the corresponding site showed a gradual decrease with the increasing dose of FAM-ZOL. Statistical significance was reached at 10 µM and 50 µM as shown in FIG. 12B.

Figure 12C:
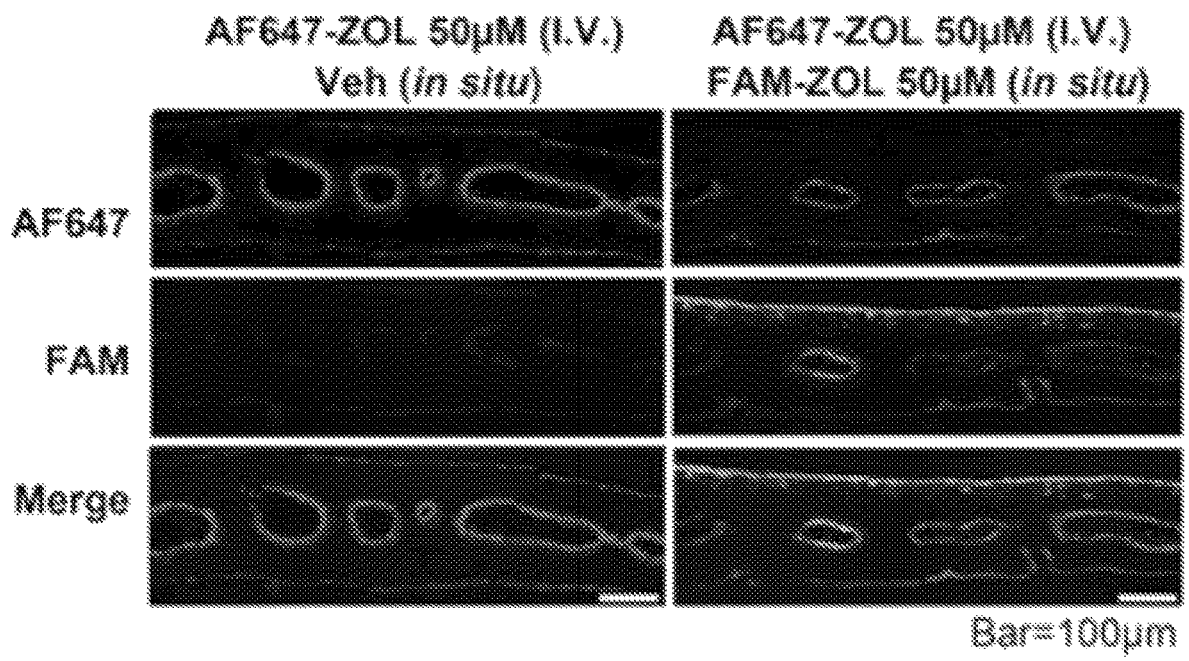

The cranial bone cryo-cross sections revealed AF647-ZOL labeling on the external and internal bone surfaces, as well as trabecular surface as shown in FIG. 12C. In the cranial bone specimen received FAM-ZOL sub-periosteal injection, a FAM-ZOL signal was observed primarily on the external bone surface and, occasionally, in the bone marrow space. The AF647-ZOL signal on the external bone surface was disproportionately reduced as compared to the internal bone surface (FIG. 12C).

Alternative Approaches

If desired, the data from the above study could be used to perform power analysis and adjust the number of animals. In addition to the proposed fluorescent biophotonics imaging method, one may use non-decalcified bone cryosection, which may provide the depth of adsorbed FL-BP in bone. Alternatively, bone pieces may be sampled and decalcified in vitro to release the adsorbed FL-BP. The released FL-BP may be quantified by 2-color-plate reader or HPLC.

Example 3

BP Displacement Therapy for the Prevention of BRONJ In Vivo

This study examines the effectiveness of the proposed BP displacement in preventing the development of BRONJ. The intraoral administration of an inactive and/or low activity FL-BP prior to tooth extraction was applied to the established ZOL-induced mouse BRONJ model. The postulated disease modification was determined by the prevalence of BRONJ, as well as histological oral mucosa abnormality and osteonecrosis development. This study establishes proof-of-concept for the proposed BP displacement therapy.

Experiment 3-1

Figure 13:
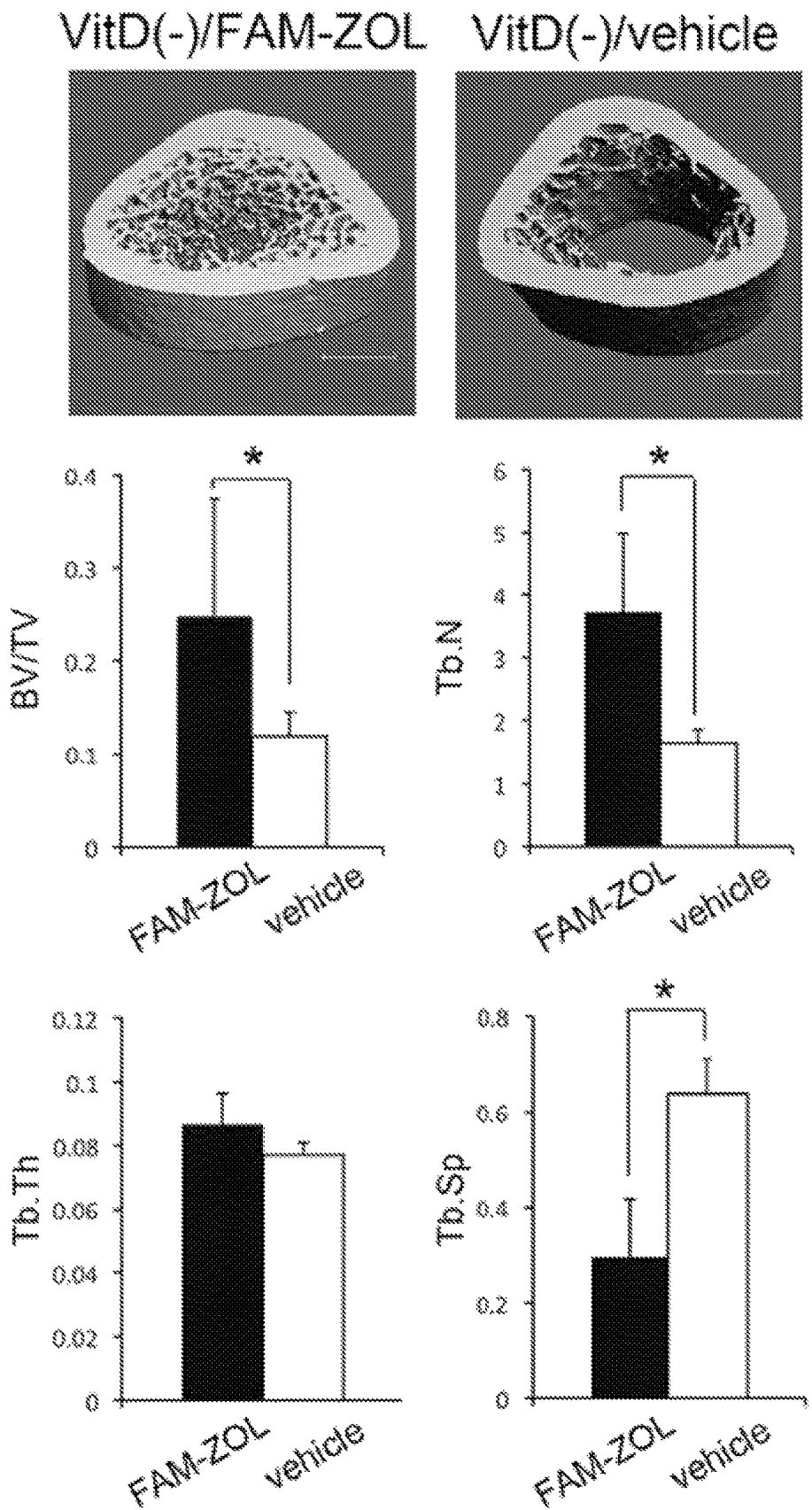
FIG. 13 shows the results of micro CT evaluation of mouse femur trabecular structure. The pharmacological function of 5-FAM-ZOL was examined in vitamin D deficient (VitD (−)) rats (n=3 in each group). 5-FAM-ZOL effectively blocked catabolic bone remodeling resulting in increased trabecular bone structure. Bars are 1.0 mm. *: p<0.05 by Student's t-test.

This study determines the anti-resorptive function of FL-BP in vivo, as compared to ZOL. Female B6 mice were injected with 50 µM ZOL (n=6), 50 µM FL-BP (n=6) or 0.9% NaCl vehicle solution (control: n=6) via tail vein. Three weeks later, mice were euthanized and femur and L4/L5 were harvested. After fixed in 10% buffered formalin, bone samples were subjected to micro CT analysis. The anti-resorptive function were quantitatively established by the trabecular bone three-dimensional morphometry (e.g., BV/TV, Tb.N, Tb.Th, TbSp). 5-FAM-ZOL developed by BioVinc exhibited pharmacological function as shown in FIG. 13. FL-BPs with minimal or no pharmacological BP function are used. As used herein, a compound that has minimal or no pharmacological BP function means that the compound exhibits little to no anti-resorptive activity as measured by a protein anti-prenylation assay (see Kashemirov (2008) Bioconjugate Chem. 19(12): 2308-2310; Sun (2016) Bioconjugate Chem. 27(2): 329-340).

Experimental Results

Mice were IV injected with 0.9% NaCl (vehicle solution), ZOL (184 µM×100=5.0 µg/animal) or AF647-ZOL (184 µM×100 µL=22.0 µg/animal) and femurs were harvested 2 weeks after injection. The micro CT data were compared.

Figure 14:
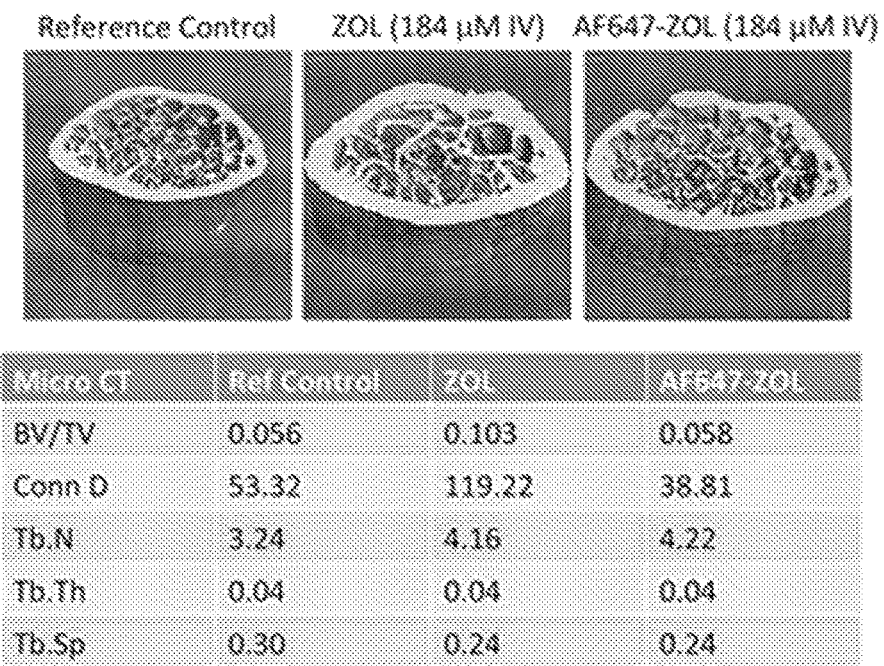
FIG. 14 shows the results of micro CT evaluation of mouse femur trabecular structure. IV injection of ZOL, but not AF647-ZOL, significantly increased bone structural parameters.

ZOL injection nearly doubled the volume of femur trabecular bone (BV/TV) and the connectivity density. By contrast, as shown in FIG. 14, AF647-ZOL did not change any of bone structural parameters. This study suggested that AF647-ZOL did not have the antiresorptive pharmacological effect of ZOL.

Experiment 3-2

Female B6 mice were treated with 200 µl of 350 µM ZOL IV injection via tail vein. The ZOL dose for mice was calculated by metabolic scaling of human dose for cancer patient. One week later, the intraoral injection FL-BP was performed at the maxillary first molar area of gingival/palatal tissue. FL-BP used in this experiment possessed equivalent bone affinity to ZOL; but significantly reduced BP function. One week after the intraoral injection, the maxillary left first molar was extraction. Mice in each group were euthanized at week 2 (n=6 in each group) and at week 4 (n=6 in each group). Maxillary tissue including the tooth extraction site, mandible, femur, and L4/L5 lumber bones were harvested. All bone samples were fixed in 10% buffered formalin and analyzed by micro CT. After decalcification by 10% EDTA, paraffin sections were used for histopathological examination. The sections with cytokeratin 14 immunohistology were examined for epithelial pathology and TRAP for osteoclast.

Figure 15:
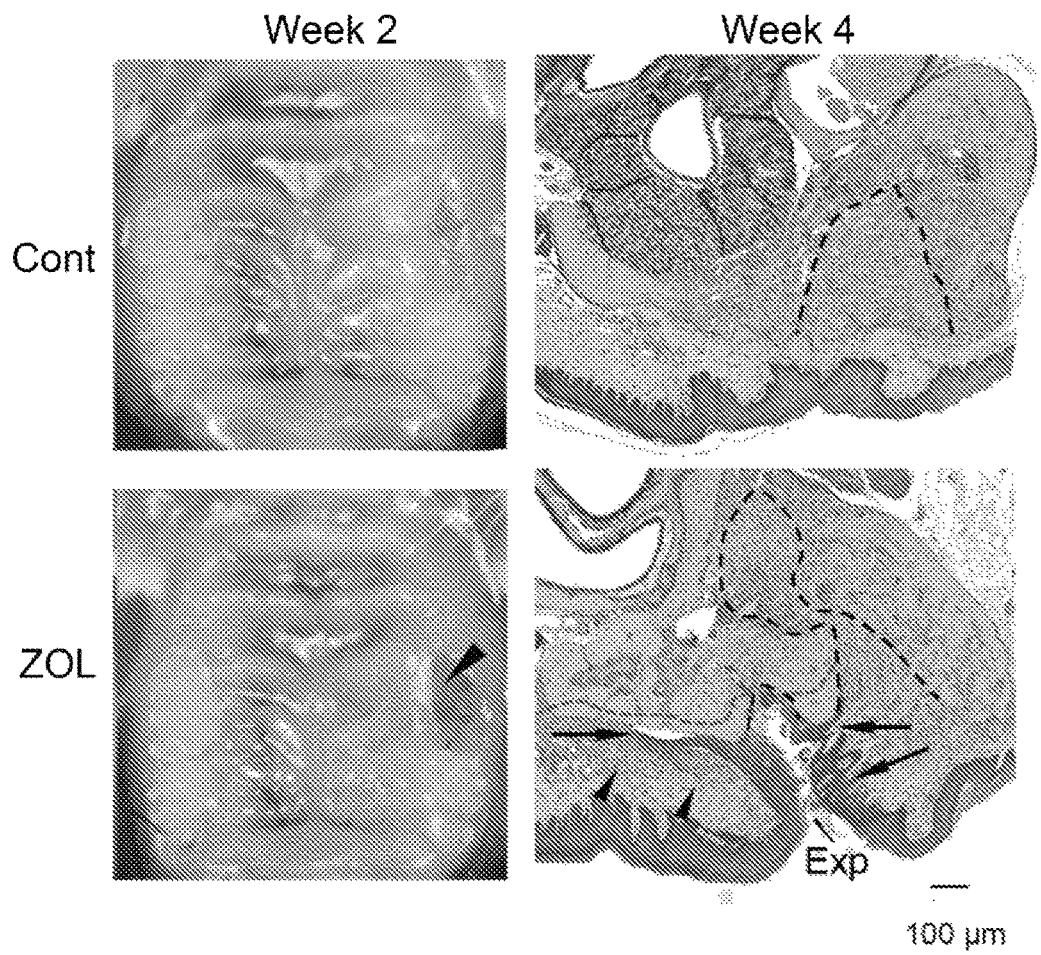
FIG. 15 are images showing that the mouse ONJ model is a suitable BRONJ model. Healing of the tooth extraction wound was delayed in the ZOL-injected mice (arrowhead). Oral epithelial hyperplasia (arrows) resulted in the exposure of necrotic alveolar bone (red dotted line, substantially horizontal, in bottom right panel).

In a preliminary study female B6 mice were injected 500 µg/Kg ZOL (equivalent to 200 µl of 350 µM ZOL) via tail vein and one week later, maxillary left first molar was extracted. Tooth extraction wound of control mice injected with vehicle solution was closed in 2 to 4 weeks, whereas 100% and 50% of ZOL-injected mice showed open oral wound at 2 weeks and 4 weeks of tooth extraction, respectively (FIG. 15).

Experimental Results

Figure 16A:
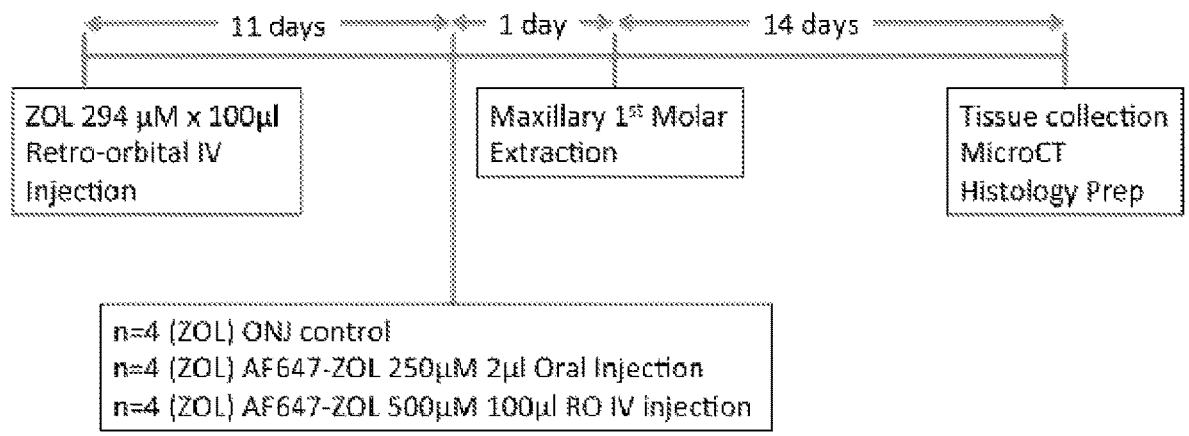
FIG. 16A to FIG. 16C demonstrate the prevention or inhibition of BRONJ in the BRONJ mouse model.

Mice received a bolus IV injection of ZOL (440 µg/Kg; 294 µM×100 µL=8.0 µg/animal) from retro-orbital venous plexus. As shown in FIG. 16A, eleven (11) days later, mice received AF647-ZOL intra-oral injection (250 µM×2 µL=0.59 µg/animal) or AF647-ZOL IV injection (500 µM×100 µL=59.2 µg/animal) and then one day after AF647-ZOL injection, mice were subjected to extraction of the left maxillary first molar and the oral wound healing was evaluated 2 weeks after tooth extraction. The AF647-ZOL signal in distant bone was assessed in femurs.

Figure 16B:
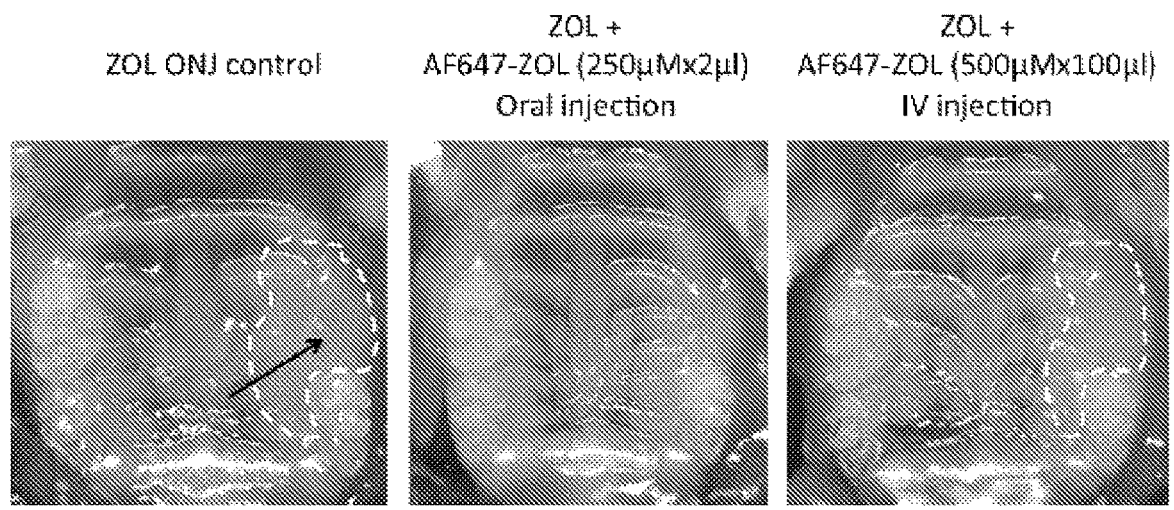
Figure 16C:
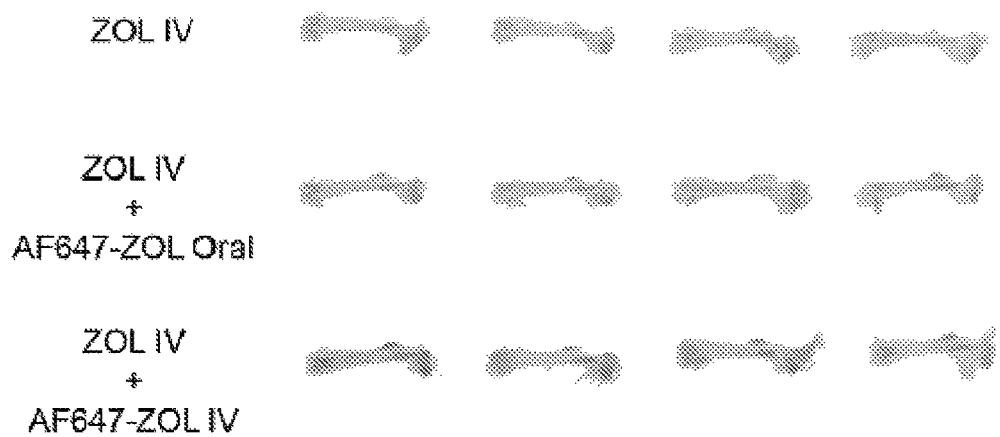

FIG. 16B shows that ZOL-injected disease control mice showed delayed wound healing with gingival swelling and jawbone exposure, consistent with the development of a BRONJ-like lesion. Intra-oral injection of AF647-ZOL 1 day before the tooth extraction resulted in the complete prevention of BRONJ without oral mucosa inflammation/swelling in all individuals (n=4) in this group. By contrast, some mice which received an AF647-ZOL IV injection showed signs of oral mucosa inflammation/swelling, although jawbone exposure was much attenuated (FIG. 16B). Evaluation of femurs demonstrated a clear AF647-ZOL signal in mice which received AF647-ZOL by IV injection but not in mice which received AF647-ZOL by intra-oral injection as shown in FIG. 16C. The outcome indicated that intra-oral application and localized BP displacement in jawbone is advantageous.

Alternative Approaches

Human ONJ cases are determined after 8 weeks of non-healing oral wound. Because mouse exhibits faster metabolism and accelerated wound healing, this study can observe tooth extraction wound for 4 weeks. By this time, control mice show complete wound healing. However, the effect of the FL-BP therapeutic intervention may need to be monitored for a longer period.

The results for the experiments with AF647-ZOL indicate that 1) Equilibrium-based BP displacement occurs in vivo, and thereby supports the therapeutic use of inactive BPs for preventing, inhibiting, and/or treating BRONJ, 2) fluorescent compounds, such as AF647, may be conjugated to a BP, and when conjugated thereto, the antiresorptive activity of the BP is reduced to a minimum, while the mineral binding efficiency is retained, and 3) intra-oral application of inactive BPs is effective in preventing, inhibiting, or treating BRONJ.

Example 4

Alkyl Bisphosphonates

Figure 17:
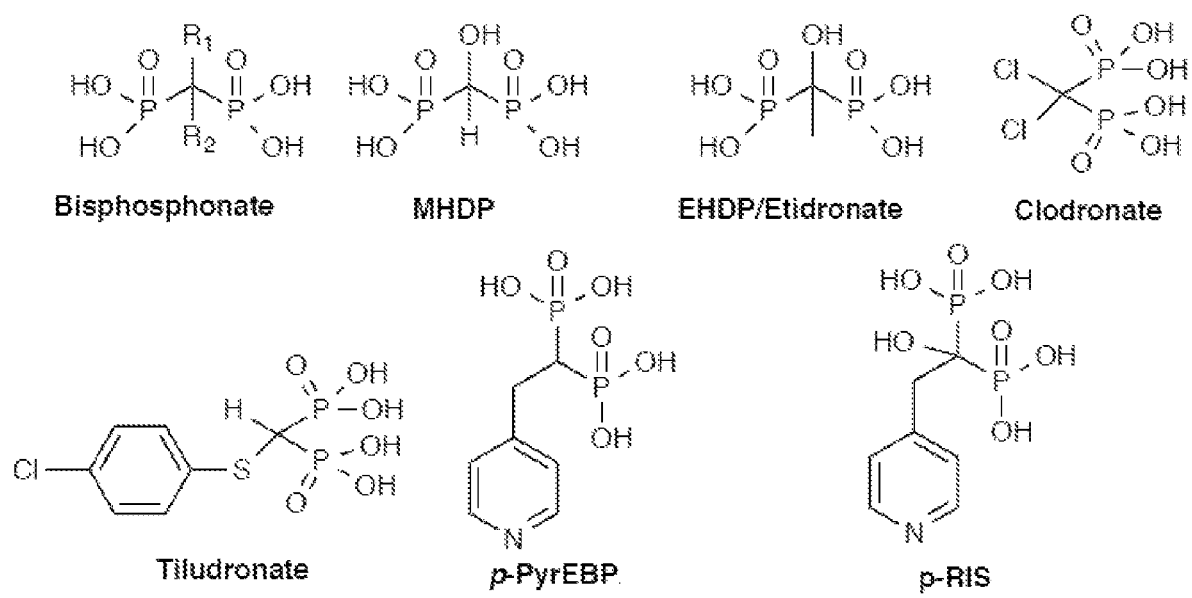
FIG. 17 shows the structural formulas of a several alkylidene bisphosphonates, including methylene hydroxyl bisphosphonate (MHDP), ethylene hydroxyl bisphosphonate (EHDP), methylene bisphosphonate (MBP), clodronate, tiludronate, 2-(pyridin-4-yl)ethane-1,1-diyl bisphosphonic acid (p-PyrEBP), and 1-hydroxy-2-(pyridin-4-yl)ethane-1,1-diyl bis(phosphonic acid) (p-RIS).

Alkyl bisphosphonates such as methylene hydroxyl bisphosphonate (MHDP or MHBP), ethylene hydroxyl bisphosphonate (EHDP), methylene bisphosphonate (MBP), clodronate, and the like (FIG. 17) may displace N-BPs in sufficient amounts to prevent, reduce, or inhibit the deleterious action of N-BPs in the jaw and other skeletal sites. The alkyl BPs can have a fluorescent compound conjugated thereto, some of which are illustrated in FIG. 18.

Figure 19A:
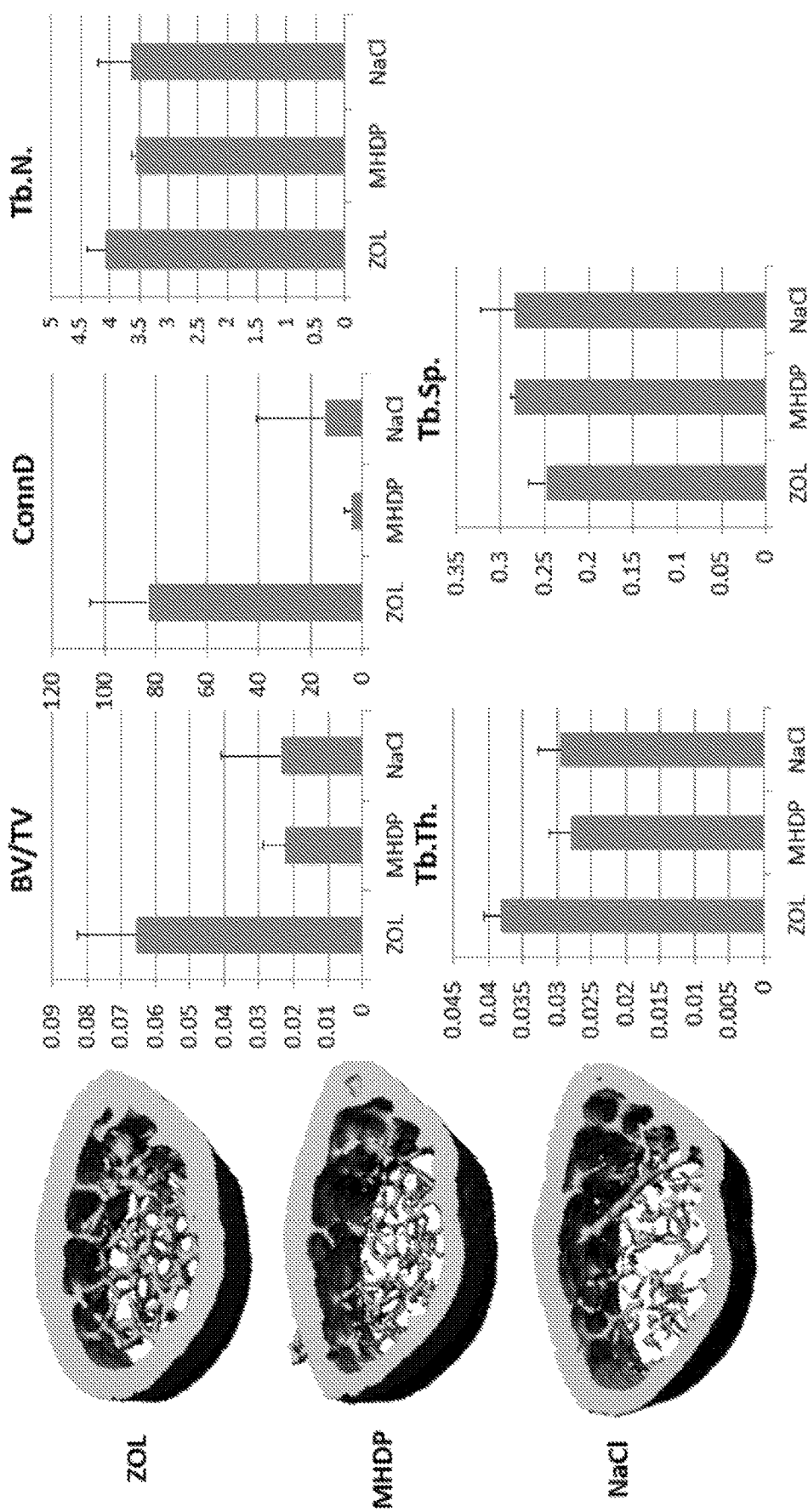
FIG. 19A to FIG. 19C present evidence that certain alkylidene bisphosphonates can be used to displace active BPs in vivo in the mouse model.

The results shown in FIG. 19A document the lack of anti-resorptive activity of MHDP, thereby indicating that such alkyl BPs can be used to treat, inhibit, reduce, or prevent BRONJ and other bone and skeletal problems caused by active BPs. Western blot analysis confirmed these results and indicated that ZOL but not MHDP and ETI (etidronate) inhibited Rap1A prenylation (accumulated unprenylated Rap1A (uRap1A)) in J774 macrophages at 10 µM and 100 µM dose.

Figure 19B:
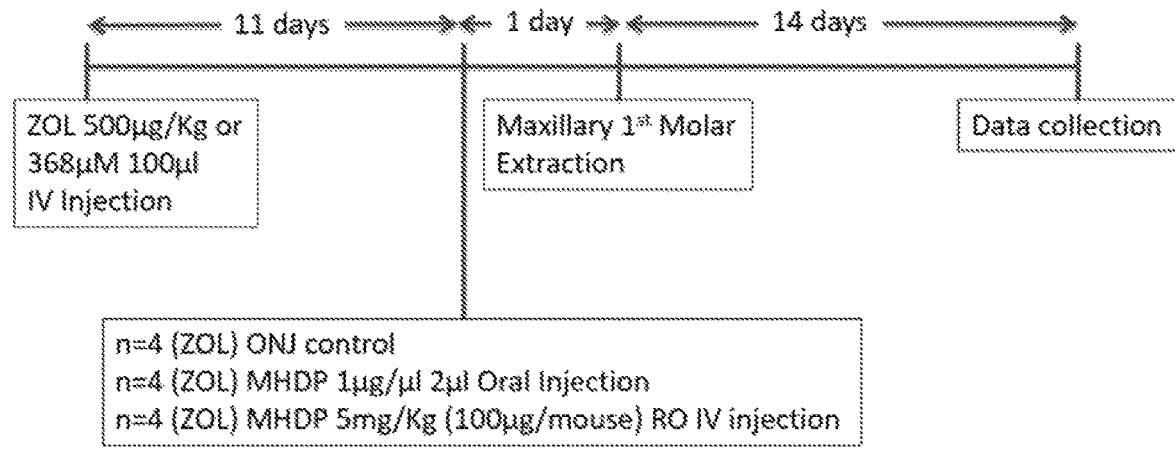
Figure 19C:
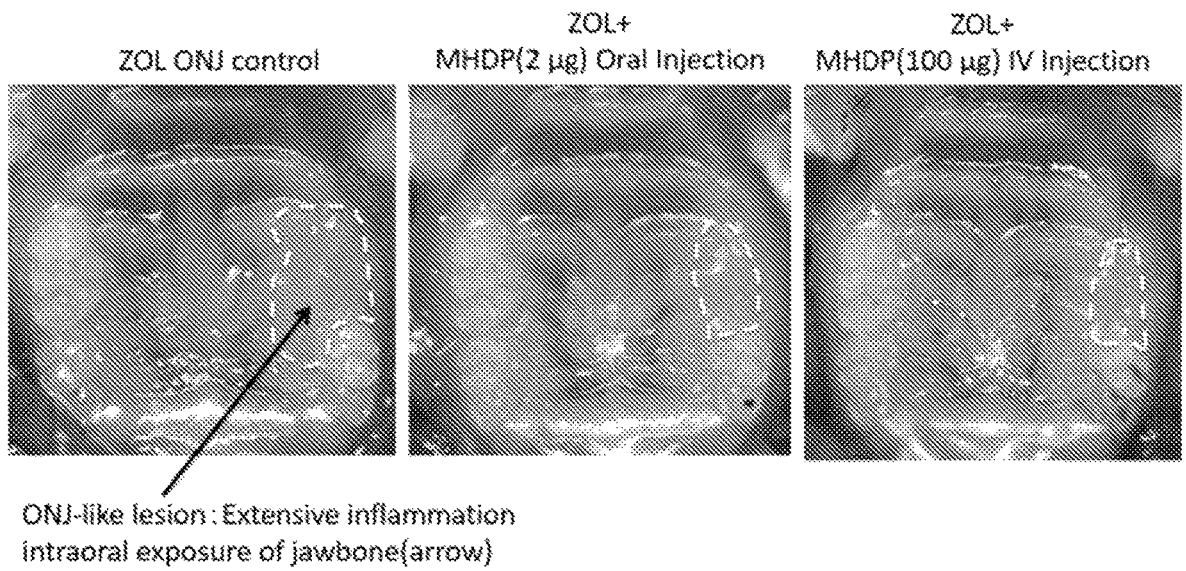
Figure 20:
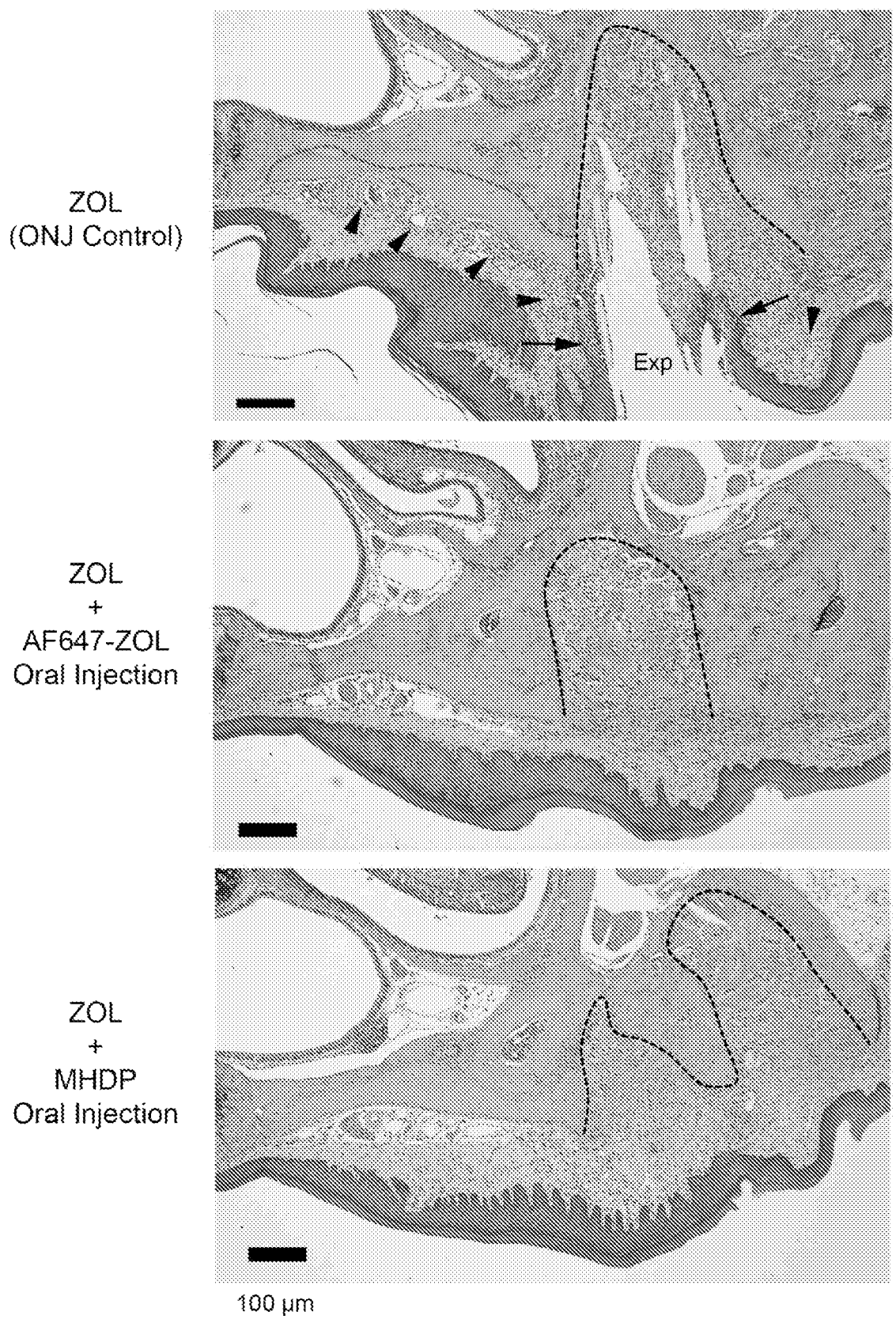
FIG. 20 shows representative histology of mouse maxilla at the tooth extraction site. ZOL-injected mice demonstrated the development of an ONJ-like lesion 2 weeks after maxillary molar extraction, highlighted by an exposed wound (Exp) flanked by oral epithelial hyperplasia (arrows). The tooth extraction socket (black dotted line) did not show bone wound healing and the surface of palatal bone (red dotted line) was non-vital (osteonecrosis), which interfaced to the localized and intense inflammatory reaction (arrowheads). ZOL-mice treated with the one time oral injection of AF647-ZOL or MHDP did not develop an ONJ-like lesion. The tooth extraction socket (black dotted line) was filled with regenerating bone and oral mucosa inflammation was much attenuated. No osteonecrosis of the maxillary bone was observed.
Figure 21:
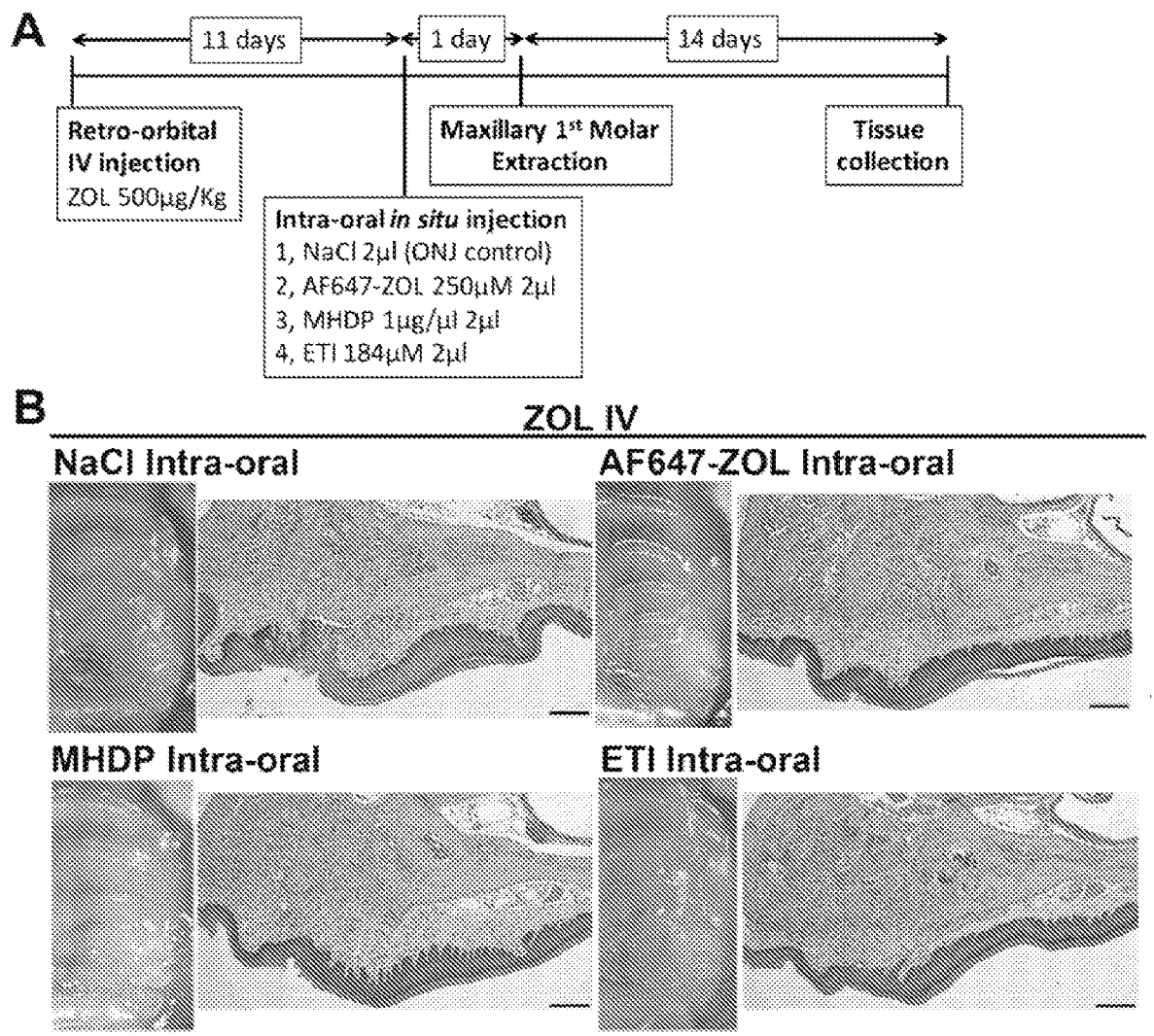
FIG. 21, Panels A and B, show ONJ prevention by intra-oral injection of inactive BPs in mice. Panel A is a diagram of the experimental time line. Mice treated by IV injection of ZOL (500 μg/kg) received an intra-oral injection of AF647-ZOL, MHDP or ETI (etidronate) one day prior to maxillary $1^{st}$ molar extraction. The development of ONJ was evaluated 14 days after tooth extraction. Panel B shows the disease control mice (ZOL-NaCl) developed ONJ-like lesions at the tooth extraction sites, which appeared to be prevented by the intra-oral injection of AF647-ZOL, MHDP or ETI.

Therefore, as schematically shown in FIG. 19B mouse maxillae were treated with ZOL and then either 2 µg of MHDP was orally injected to the site of the molar to be extracted or 100µg of MHDP was IV injected and the sites of molar extraction of treated mouse maxilla were compared to controls. As shown in FIG. 19C, intra-oral injection and IV injection of MHDP prevented the development of ONJ-like lesions as compared to the untreated controls.

Example 5

Near Infrared FL-BPs

Figure 4:
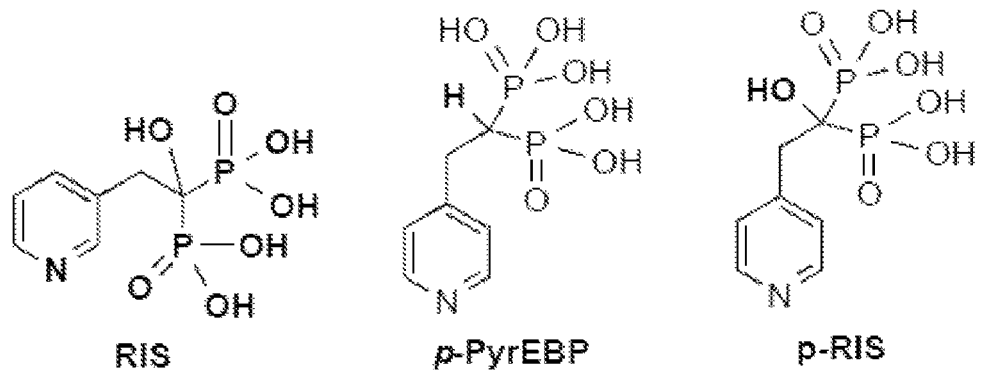
FIG. 4 shows the structure of RIS, 2-(pyridin-4-yl)ethane-1,1-diylbisphosphonic acid (p-PyrEBP), and 1-hydroxy-2-(pyridin-4-yl)ethane-1,1-diylbis(phosphonic acid) (p-RIS).
Figure 5B:
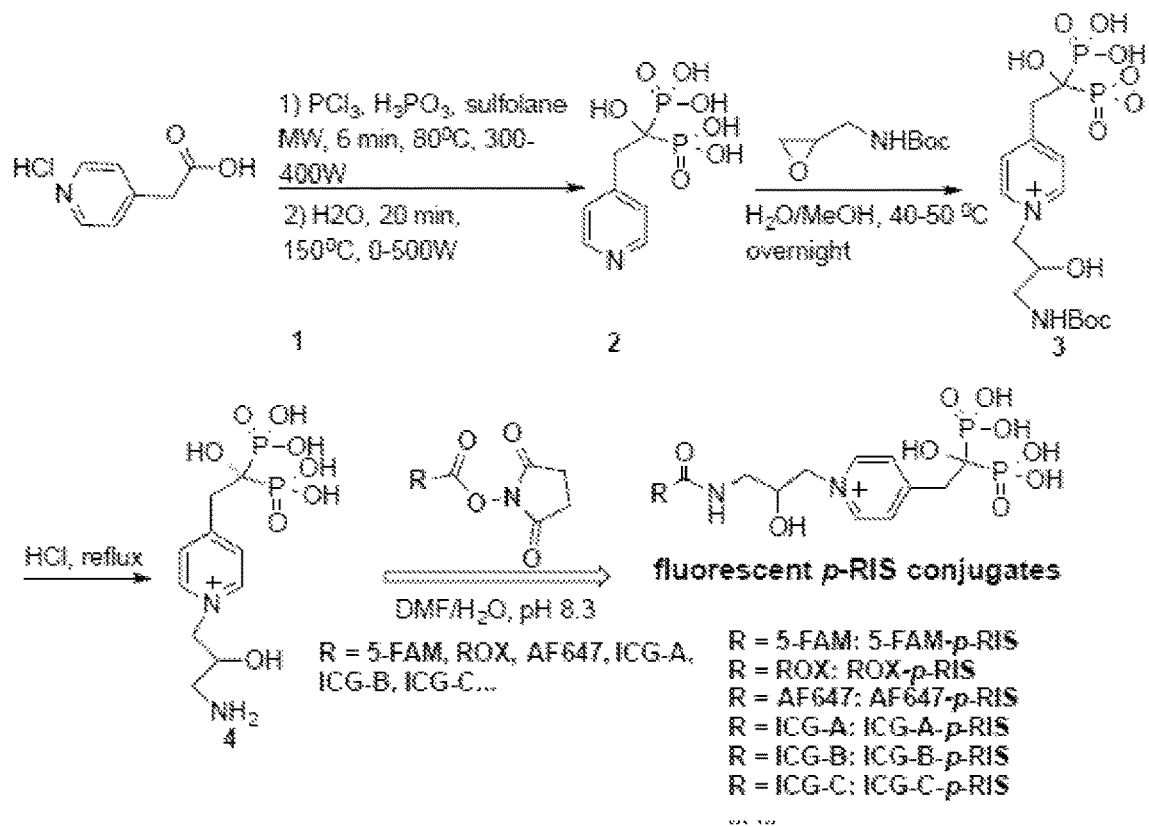

Near infrared (NIR) FL-BPs were synthesized as novel theranostic agents (FIG. 18): specifically, the indocyanine green-BP (ICG-BP) conjugates: the fluorophore ICG attached to p-PyrEBP or p-RIS (FIG. 4). Unlike the potent antiresorptive N-BPs RIS or ZOL, the BP scaffolds of p-PyrEBP and p-RIS either lack an α-hydroxy group and/or its pyridyl side chain are be para-substituted, which will decrease antiresorptive activity to a negligible level, with only a minor effect on bone affinity. The design thus allows the FL-BP conjugates to be strongly adsorbed to the surface of hydroxyapatite, while not exhibiting the biological activities of the parent N-BPs.

ICG, the only clinically approved NIR fluorescent dye for human use, absorbs around 800 nm and fluoresces in the NIR region (600-1200 nm) with high fluorescence intensity, and has been used widely in imaging studies involving the heart, liver, lungs, blood circulation, and lymph nodes. An imaging system (Xiralite X4, Mivenion GmbH, Berlin, Germany) has recently been approved for use in the US, and the hand-held instruments (e.g., KaVo DIAGNOcam) are currently being used to identify caries in teeth using NIR wavelength light, which are readily adaptable to the ICG-BPs here. Thus, this novel composition of matter allows ease of visualization of BPs without antiresorptive effects in bone.

However, ICG does not possess any native functionality that would permit linkages. Thus, a carboxyl moiety was introduced into the molecule, in such a way that conjugation with a BP is possible at three alternative positions. These scaffolds are designed to have minimal effect on the fluorophore core, preserving the optical properties of the ICG fluorophore (FIG. 18).

These novel ICG-BPs can be used to allow safe dental procedures to be carried out in any patient undergoing BP therapy for osteoporosis, including highly dosed N-BPs in cancer associated bone disease. Ideally, the product can lead to minimal systemic adsorption of the FL-BP, while allowing a dentist to use an inexpensive hand-held light to visibly ascertain effective dosing at the jawbone site and then initiate the dental procedure. The use of NIR fluorescent conjugates is a key innovation because it allows the visualization of the maxillofacial bone through the overlaying fascia and tissue to allow monitoring for patient variation in conjugate uptake, such as might be due to differential jawbone turnover levels depending on such individual patent characteristics age, gender, ethnicity (personalized or precision medicine). This improves ease of use and increases cost effectiveness, while increasing the confidence of the dentist in the outcome of the procedure, due to the ability to observe directly the loading of the theranostic agent.

REFERENCES

In addition to the references cited throughout, which are herein incorporated by reference in their entirety, the following references are also incorporated herein by reference in their entirety:

1. Ruggiero S L, Mehrotra B, Rosenberg T J, Engroff S L. Osteonecrosis of the jaws associated with the use of bisphosphonates: a review of 63 cases. Journal of Oral and Maxillofacial Surgery: Official Journal of the American Association of Oral and Maxillofacial Surgeons. 2004; 62(5):527-34. Epub 2004/05/04. PubMed PMID: 15122554.
2. Reid I R, Cornish J. Epidemiology and pathogenesis of osteonecrosis of the jaw. Nat Rev Rheumatol. 2012; 8(2):90-6. doi: Doi 10.1038/Nrrheum.2011.181. PubMed PMID: WOS:000300408900009.
3. Barasch A, Cunha-Cruz J, Curro F A, Hujoel P, Sung A H, Vena D, Voinea-Griffin A E, Grp C C. Risk Factors for Osteonecrosis of the Jaws: A Case-Control Study from the CONDOR Dental PBRN. J Dent Res. 2011; 90(4):439-44. doi: Doi 10.1177/0022034510397196. PubMed PMID: WOS:000288798600007.
4. Ruggiero S L, Dodson T B, Fantasia J, Goodday R, Aghaloo T, Mehrotra B, O'Ryan F. American Association of Oral and Maxillofacial Surgeons position paper on medication-related osteonecrosis of the jaw—2014 update. Journal of Oral and Maxillofacial Surgery: Official Journal of the American Association of Oral and Maxillofacial Surgeons. 2014; 72(10):1938-56. doi: 10.1016/j.joms.2014.04.031. PubMed PMID: 25234529.
5. Hokugo A, Sun S T, Park S, McKenna C E, Nishimura I. Equilibrium-dependent bisphosphonate interaction with crystalline bone mineral explains anti-resorptive pharmacokinetics and prevalence of osteonecrosis of the jaw in rats. Bone. 2013; 53(1):59-68. doi: Doi 10.1016/J.Bone.2012.11.030. PubMed PMID: WOS:000314257100010.
6. Russell R G G, Watts N B, Ebetino F H, Rogers M J. Mechanisms of action of bisphosphonates: similarities and differences and their potential influence on clinical efficacy. Osteoporosis Int. 2008; 19(6):733-59. doi: Doi 10.1007/S00198-007-0540-8. PubMed PMID: WOS:000257382200002.
7. Lewiecki E M. RANK ligand inhibition with denosumab for the management of osteoporosis. Expert Opin Biol Th. 2006; 6(10):1041-50. doi: Doi 10.1517/14712598.6.10.1041. PubMed PMID: WOS:000240907100009.
8. Yonemori K, Fujiwara Y, Minami H, Kitagawa K, Fujii H, Arai T, Sohn W, Ohkura M, Ohtsu T. Phase 1 trial of denosumab safety, pharmacokinetics, and pharmacodynamics in Japanese women with breast cancer-related bone metastases. Cancer Sci. 2008; 99(6):1237-42. doi: Doi 10.1111/J.1349-7006.2008.00803.X. PubMed PMID: WOS:000255906200022.
9. Malan J, Ettinger K, Naumann E, Beirne O R. The relationship of denosumab pharmacology and osteonecrosis of the jaws. Or Surg or Med or Pa. 2012; 114(6):671-6. doi: Doi 10.1016/J.Oooo.2012.08.439. PubMed PMID: WOS:000311370000013.
10. Brown J P, Morin S, Leslie W, Papaioannou A, Cheung A M, Davison K S, Goltzman D, Hanley D A, Hodsman A, Josse R, Jovaisas A, Juby A, Kaiser S, Karaplis A, Kendler D, Khan A, Ngui D, Olszynski W, Ste-Marie L G, Adachi J. Bisphosphonates for treatment of osteoporosis Expected benefits, potential harms, and drug holidays. Can Fam Physician. 2014; 60(4):324-33. PubMed PMID: WOS:000335649800015.
11. Flichy-Fernandez A J, Gonzalez-Lemonnier S, Balaguer-Martinez J, Penarrocha-Oltra D, Penarrocha-Diago M A, Bagan-Sebastian J V. Bone necrosis around dental implants: A patient treated with oral bisphosphonates, drug holiday and no risk according to serum CTX. Journal of Clinical and Experimental Dentistry. 2012; 4(1):e82-5. Epub 2012/02/01. doi: 10.4317/jced.50698. PubMed PMID: 24558532; PubMed Central PMCID: PMC3908817.
12. Hutcheson A, Cheng A, Kunchar R, Stein B, Sambrook P, Goss A. A C-terminal crosslinking telopeptide test-based protocol for patients on oral bisphosphonates requiring extraction: a prospective single-center controlled study. Journal of Oral and Maxillofacial Surgery: Official Journal of the American Association of Oral and Maxillofacial Surgeons. 2014; 72(8):1456-62. Epub 2014/05/06. doi: 10.1016/j.joms.2014.02.036. PubMed PMID: 24793621.
13. Ebetino F H, Hogan A M, Sun S, Tsoumpra M K, Duan X, Triffitt J T, Kwaasi A A, Dunford J E, Barnett B L, Oppermann U, Lundy M W, Boyde A, Kashemirov B A, McKenna C E, Russell R G. The relationship between the chemistry and biological activity of the bisphosphonates. Bone. 2011; 49(1):20-33. doi: 10.1016/j.bone.2011.03.774. PubMed PMID: 21497677.
14. Kashemirov B A, Bala J L, Chen X, Ebetino F H, Xia Z, Russell R G G, Coxon F P, Roelofs A J, Rogers M J, McKenna C E. Fluorescently labeled risedronate and related analogues: "magic linker" synthesis. Bioconjug Chem. 2008; 19(12):2308-10. doi: 10.1021/bc800369c. PubMed PMID: 19032080.
15. Ruggiero S L, Dodson T B, Assael L A, Landesberg R, Marx R E, Mehrotra B. American Association of Oral and Maxillofacial Surgeons position paper on bisphosphonate-related osteonecrosis of the jaws—2009 update. Journal of Oral and Maxillofacial Surgery: Official Journal of the American Association of Oral and Maxillofacial Surgeons. 2009; 67(5 Suppl):2-12. Epub 2009/04/25. doi: 10.1016/j.joms.2009.01.009. PubMed PMID: 19371809.
16. FDA background document for meeting of advisory committee for reproductive health drugs and drug safety and risk management advisory committee 2014 (cited November 2014) FDA background document for meeting of advisory committee for reproductive health drugs and drug safety and risk management advisory committee). Available from: WorldWideWeb.fda.gov/downloads/AdvisoryCommittees/CommitteesMeetingMaterials/d rugs/DrugSafetyandRiskManagementAdvisoryCommittee/ucm270958.pdf, where "WorldWideWeb" is "www".
17. Sun S T, Blazewska K M, Kashemirov B A, Roelofs A J, Coxon F P, Rogers M J, Ebetino F H, McKenna M J, McKenna C E. Synthesis and Characterization of Novel Fluorescent Nitrogen-Containing Bisphosphonate Imaging Probes for Bone Active Drugs. Phosphorus Sulfur.

18. Roelofs A J, Boyde A, Lundy M W, McKenna C E, Blazewska K, Sun S T, Kashemirov B A, Russell R G G, Ebetino F H, Rogers M J, Coxon F P. Bone mineral affinity influences the distribution of a bisphosphonate and a lower affinity analogue in vivo. Bone. 2009; 44(2): S430-S1. doi: Doi 10.1016/J.Bone.2009.03.377. PubMed PMID: WOS:000266348600587.
19. Roelofs A J, Coxon F P, Ebetino F H, Lundy M W, Henneman Z J, Nancollas G H, Sun S, Blazewska K M, Bala J L, Kashemirov B A, Khalid A B, McKenna C E, Rogers M J. Fluorescent risedronate analogues reveal bisphosphonate uptake by bone marrow monocytes and localization around osteocytes in vivo. J Bone Miner Res. 2010; 25(3):606-16. doi: 10.1359/jbmr.091009. PubMed PMID: 20422624.
20. Roelofs A J, Stewart C A, Sun S T, Blazewska K M, Kashemirov B A, McKenna C E, Russell RGG, Rogers M J, Lundy M W, Ebetino F H, Coxon F P. Influence of Bone Affinity on the Skeletal Distribution of Fluorescently Labeled Bisphosphonates In vivo. J Bone Miner Res. 2012; 27(4):835-47. doi: Doi 10.1002/Jbmr.1543. PubMed PMID: ISI:000301708100013.
21. Turek J, Ebetino F H, Lundy M W, Sun S T, Kashemirov B A, McKenna C E, Gallant M A, Plotkin L I, Bellido T, Duan X C, Triffitt J T, Russell RGG, Burr D B, Allen M R. Bisphosphonate Binding Affinity Affects Drug Distribution in Both Intracortical and Trabecular Bone of Rabbits. Calcified Tissue Int. 2012; 90(3):202-10. doi: Doi 10.1007/S00223-012-9570-0. PubMed PMID: ISI: 000301796200005.
22. Vermeer J A, Jansen I D, Marthi M, Coxon F P, McKenna C E, Sun S, de Vries T J, Everts V. Jaw bone marrow-derived osteoclast precursors internalize more bisphosphonate than long-bone marrow precursors. Bone. 2013; 57(1):242-51. Epub 2013/08/22. doi: 10.1016/j.bone.2013.08.007. PubMed PMID: 23962725.
23. Cheong S, Sun S, Kang B, Bezouglaia O, Elashoff D, McKenna C E, Aghaloo T L, Tetradis S. Bisphosphonate Uptake in Areas of Tooth Extraction or Periapical Disease. J Oral Maxil Surg. 2014.
24. Bae S, Sun S, Aghaloo T, Oh J E, McKenna C E, Kang M K, Shin K H, Tetradis S, Park N H, Kim R H. Development of oral osteomucosal tissue constructs in vitro and localization of fluorescently-labeled bisphosphonates to hard and soft tissue. International journal of molecular medicine. 2014; 34(2):559-63. Epub 2014/06/13. doi: 10.3892/ijmm.2014.1802. PubMed PMID: 24920042; PubMed Central PMCID: PMC4094592.
25. Marma M S, Xia Z D, Stewart C, Coxon F, Dunford J E, Baron R, Kashemirovli B A, Ebetino F H, Triffitt J T, Russell RGG, McKenna C E. Synthesis and biological evaluation of alpha-halogenated bisphosphonate and phosphonocarboxylate analogues of risedronate. Journal of Medicinal Chemistry. 2007; 50(24):5967-75. doi: Doi 10.1021/Jm0702884. PubMed PMID: ISI: 000251181900013.
26. McKenna C E, Kashemirov B A, Bala J L, inventors; University of Southern California, assignee. Synthesis of drug conjugates via reaction with epoxide-containing linkers. USA patent U.S. Pat. No. 8,431,714 B2. 2013 Apr. 30.
27. Sun S T. Fluorescent imaging probes of nitrogen-containing bone active drugs: design, synthesis and applications. Los Angeles, Calif.: University of Southern California; 2013.
28. Duan X. Physiological and biological mechanisms of bisphosphonate action: University of Oxford; 2010.
29. Xiu Y, Xu H, Zhao C, Li J, Morita Y, Yao Z, Xing L, Boyce B F. Chloroquine reduces osteoclastogenesis in murine osteoporosis by preventing TRAF3 degradation. The Journal of clinical investigation. 2014; 124(1):297-310. Epub 2013/12/10. doi: 10.1172/JCI66947. PubMed PMID: 24316970; PubMed Central PMCID: PMC3871219.

All scientific and technical terms used in this application have meanings commonly used in the art unless otherwise specified.

As used herein, the terms "subject" and "patient" are used interchangeably and include humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

The phrase "comprises, consists essentially of, or consists of" is used as a tool to avoid excess page and translation fees and means that in some embodiments the given thing at issue comprises something, and in some embodiments the given thing at issue consists of something. For example, the sentence "In some embodiments, the composition comprises, consists essentially of, or consists of A" is to be interpreted as if written as the following two separate sentences: "In some embodiments, the composition comprises A. In some embodiments, the composition consists essentially of A. In some embodiments, the composition consists of A." Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C." As used herein, the phrase "consists essentially of" in the context of a composition comprising one or more inactive BPs means the composition does not contain any active BPs, but may contain other active ingredients, e.g., an analgesic, an antibacterial, etc.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of removing or displacing an active bisphosphonate in a skeletal tissue, which comprises administering to the skeletal tissue one or more inactive bisphosphonates, wherein the one or more inactive bisphosphonates has a molecular scaffold that (a) lacks an α-hydroxy group, (b) has a pyridyl side chain that is para-substituted, or (c) lacks an α-hydroxy group and has a pyridyl side chain that is para-substituted.

2. The method according to claim 1, wherein the one or more inactive bisphosphonates has a detectable label attached thereto.

3. The method according to claim 1, wherein the one or more inactive bisphosphonates comprises a bisphosphonate conjugated to a fluorescent compound.

4. The method according to claim 3, wherein the fluorescent compound is selected from the group consisting of: ROX, FAM, AF647, ICG, ICG analogs, Cy5, Sulfo-Cy5, Cy7, and IRDye 800CW.

5. The method according to claim 3, wherein the one or more inactive bisphosphonates is selected from the group consisting of: 5-FAM-dRIS, 5(6)-FAM-dRIS, 5(6)-RhR-dRIS, and ICG-p-pyrEBP.

6. The method according to claim 3, wherein the one or more inactive bisphosphonates is ICG-A-p-PyrEBP, ICG-B-p-PyrEBP, ICG-C-p-PyrEBP, ICG-D-p-PyrEBP, ICG-A-p-RIS, ICG-C-p-RIS, or ICG-D-p-RIS.

7. The method according to claim 1, wherein the active bisphosphonate is an active nitrogen-containing bisphosphonate.

8. The method according to claim 7, wherein the active nitrogen-containing bisphosphonate is alendronate, ibandronate, minodronate, pamidronate, risedronate, or zoledronate.

9. The method according to claim 1, wherein the active bisphosphonate in the skeletal tissue is removed or displaced in vivo in a subject.

10. The method according to claim 9, wherein the one or more inactive bisphosphonates is locally administered to the subject.

11. The method according to claim 9, wherein the one or more inactive bisphosphonates is administered orally to the subject.

12. The method according to claim 9, wherein the one or more inactive bisphosphonates is administered to a gingival tissue and/or a palatal tissue of the subject.

13. The method according to claim 9, wherein the one or more inactive bisphosphonates is administered by intraoral application to a site of a dentoalveolar procedure.

14. The method according to claim 13, wherein the one or more inactive bisphosphonates is administered before, during, and/or after the dentoalveolar procedure.

15. The method according to claim 1, wherein an effective amount of the one or more inactive bisphosphonates is administered.

16. The method according to claim 1, wherein the one or more inactive bisphosphonates is administered in the form of a liposomal formulation or a nanovesicle formulation, preferably a deformable nanovesicle formulation.

17. A method of treating, reducing, preventing, or inhibiting Bisphosphonate Related Osteonecrosis of the Jaw (BRONJ) or a bisphosphonate-related symptom in a subject, which comprises administering to the subject a therapeutically effective amount of one or more inactive bisphosphonates, wherein the one or more inactive bisphosphonates has a molecular scaffold that (a) lacks an α-hydroxy group, (b) has a pyridyl side chain that is para-substituted, or (c) lacks an α-hydroxy group and has a pyridyl side chain that is para-substituted.

18. The method according to claim 17, wherein the subject has been or is being treated with an active bisphosphonate.

19. The method according to claim 17, wherein the one or more inactive bisphosphonates are selected from the group consisting of: 5(6)-FAM-dRIS, 5(6)-RhR-dRIS, 5-FAM-dRIS, 5-FAM-p-RIS, 800CW-p-pyrEBP, 800CW-p-RIS, AF647-p-RIS, clodronate, ICG-A-p-pyrEBP, ICG-A-p-RIS, ICG-B-p-pyrEBP, ICG-B-p-RIS, ICG-C-p-pyrEBP, ICG-C-p-RIS, ICG-D-p-pyrEBP, ICG-D-p-RIS, ICG-p-pyrEBP, MBP, p-PyrEBP, p-PyrEBP, p-RIS, ROX-p-RIS, and tiludronate.

20. The method according to claim 1, wherein the one or more inactive bisphosphonates is selected from the group consisting of: 5-FAM-p-RIS, 800CW-p-pyrEBP, 800CW-p-RIS, AF647-p-RIS, clodronate, MBP, p-PyrEBP, p-PyrEBP, p-RIS, ROX-p-RIS, and tiludronate.

* * * * *